(12) United States Patent
Hibner

(10) Patent No.: US 8,038,627 B2
(45) Date of Patent: *Oct. 18, 2011

(54) BIOPSY DEVICE WITH TRANSLATING VALVE MECHANISM

(75) Inventor: John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/685,721

(22) Filed: Jan. 12, 2010

(65) Prior Publication Data

US 2010/0113971 A1   May 6, 2010

Related U.S. Application Data

(63) Continuation of application No. 11/344,879, filed on Feb. 1, 2006, now Pat. No. 7,662,109, and a continuation-in-part of application No. 11/198,558, filed on Aug. 5, 2005.

(51) Int. Cl.
*A61B 10/00* (2006.01)
(52) U.S. Cl. ........................................... 600/568
(58) Field of Classification Search .......... 600/562–568; 604/160
See application file for complete search history.

(56) References Cited

U.S. PATENT DOCUMENTS

| | | |
|---|---|---|
| 3,630,192 A | 12/1971 | Jamshidi |
| 4,051,852 A | 10/1977 | Villari |
| 4,600,014 A | 7/1986 | Beraha |
| 4,782,833 A | 11/1988 | Einhorn |
| 5,234,000 A | 8/1993 | Hakky et al. |
| 5,406,959 A | 4/1995 | Mann |
| 5,439,457 A | 8/1995 | Yoon |
| 5,526,822 A | 6/1996 | Burbank et al. |
| 5,601,585 A | 2/1997 | Banik et al. |
| 5,645,209 A | 7/1997 | Green et al. |
| 5,649,547 A | 7/1997 | Ritchart et al. |
| 5,769,086 A | 6/1998 | Ritchart et al. |
| 5,775,333 A | 7/1998 | Burbank et al. |

(Continued)

FOREIGN PATENT DOCUMENTS

EP   0 995 400   4/2000

(Continued)

OTHER PUBLICATIONS

U.S. Appl. No. 60/874,792, filed Dec. 13, 2006, Hibner.

(Continued)

*Primary Examiner* — Brian Szmal
(74) *Attorney, Agent, or Firm* — Frost Brown Todd LLC

(57) ABSTRACT

A biopsy device comprises a cannula having a transverse tissue receiving aperture and a cutter that is movable relative to the cannula to sever tissue protruding through the aperture. A first valve assembly comprises a first valve body and a first actuator. The first valve body has a first port, a second port, and a third port. The first port is in fluid communication with either atmospheric air or a pressurized medium. The second port is in fluid communication with the cannula. The third port is in fluid communication with a vacuum source. The first actuator is translatable relative to the first valve body to selectively couple either the first port or the third port with the second port. An optional second valve assembly is operable to selectively couple the cannula with either a source of saline or the first valve assembly.

20 Claims, 21 Drawing Sheets

U.S. PATENT DOCUMENTS

| | | | |
|---|---|---|---|
| 5,876,329 | A | 3/1999 | Harhen |
| 5,928,164 | A | 7/1999 | Burbank et al. |
| 5,964,716 | A | 10/1999 | Gregoire et al. |
| 5,980,469 | A | 11/1999 | Burbank et al. |
| 6,007,316 | A | 12/1999 | Bandoh |
| 6,017,316 | A | 1/2000 | Ritchart et al. |
| 6,077,230 | A | 6/2000 | Gregoire et al. |
| 6,083,177 | A | 7/2000 | Kobren et al. |
| 6,086,544 | A | 7/2000 | Hibner et al. |
| 6,120,462 | A | 9/2000 | Hibner et al. |
| 6,142,946 | A | 11/2000 | Hwang et al. |
| 6,213,957 | B1 | 4/2001 | Milliman et al. |
| 6,228,055 | B1 | 5/2001 | Foerster et al. |
| 6,231,522 | B1 | 5/2001 | Voegele et al. |
| 6,273,862 | B1 | 8/2001 | Privitera et al. |
| 6,402,701 | B1 | 6/2002 | Kaplan et al. |
| 6,428,486 | B2 | 8/2002 | Ritchart et al. |
| 6,485,436 | B1 | 11/2002 | Truckai et al. |
| 6,527,731 | B2 | 3/2003 | Weiss et al. |
| 6,544,194 | B1 | 4/2003 | Kortenbach |
| 6,620,111 | B2 | 9/2003 | Stephens et al. |
| 6,638,235 | B2 | 10/2003 | Miller et al. |
| 6,659,338 | B1 | 12/2003 | Dittmann et al. |
| 6,758,824 | B1 | 7/2004 | Miller |
| 6,849,080 | B2 | 2/2005 | Lee et al. |
| 7,025,098 | B2 | 4/2006 | Osborne |
| 7,025,732 | B2 | 4/2006 | Thompson et al. |
| 7,226,424 | B2 | 6/2007 | Ritchart |
| 7,276,032 | B2 | 10/2007 | Hibner |
| 7,419,472 | B2 | 9/2008 | Hibner et al. |
| 7,445,739 | B2 | 11/2008 | Tsonton et al. |
| 7,470,237 | B2 | 12/2008 | Beckman et al. |
| 7,575,556 | B2 | 8/2009 | Speeg et al. |
| 7,662,109 | B2 * | 2/2010 | Hibner ............ 600/568 |
| 7,867,173 | B2 * | 1/2011 | Hibner et al. ....... 600/568 |
| 2002/0082518 | A1 | 6/2002 | Weiss et al. |
| 2002/0082519 | A1 | 6/2002 | Miller et al. |
| 2002/0120212 | A1 | 8/2002 | Ritchart et al. |
| 2003/0199753 | A1 | 10/2003 | Hibner et al. |
| 2004/0153003 | A1 | 8/2004 | Cicenas et al. |
| 2005/0049521 | A1 | 3/2005 | Miller et al. |
| 2005/0065453 | A1 | 3/2005 | Shabaz et al. |
| 2005/0165328 | A1 | 7/2005 | Heske et al. |
| 2005/0215922 | A1 | 9/2005 | Tsonton et al. |
| 2006/0041230 | A1 | 2/2006 | Davis |
| 2006/0074342 | A1 | 4/2006 | Hibner |
| 2006/0074343 | A1 | 4/2006 | Hibner |
| 2006/0074344 | A1 | 4/2006 | Hibner |
| 2006/0074345 | A1 | 4/2006 | Hibner et al. |
| 2006/0258955 | A1 | 11/2006 | Hoffman et al. |
| 2007/0032742 | A1 | 2/2007 | Monson et al. |
| 2007/0032743 | A1 | 2/2007 | Hibner |
| 2007/0112751 | A1 | 5/2007 | Pyun |
| 2007/0213630 | A1 | 9/2007 | Beckman et al. |
| 2007/0239067 | A1 | 10/2007 | Hibner et al. |
| 2008/0004545 | A1 | 1/2008 | Garrison |
| 2008/0195066 | A1 | 8/2008 | Speeg et al. |
| 2008/0312554 | A1 | 12/2008 | Garrison |

FOREIGN PATENT DOCUMENTS

| | | |
|---|---|---|
| EP | 1 520 518 | 4/2005 |
| EP | 1 832 234 | 12/2007 |
| EP | 1 932 482 | 6/2008 |
| GB | 2 018 601 | 10/1979 |
| RU | 2021770 | 10/1994 |
| WO | WO 03/077768 | 9/2003 |
| WO | WO 2004/052212 | 6/2004 |
| WO | WO 2004/075728 | 9/2004 |
| WO | WO 2006/005342 | 1/2006 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

U.S. Appl. No. 60/869,736, filed Dec. 13, 2006, Hibner.

EnCor™ *MRI* Specifications and Breast Biopsy System, SenoRx, 2005, p. 102.

European Search Report dated Jun. 13, 2007 for Application No. 07250402.0.

European Search Report dated Nov. 14, 2007 for Application No. 07250926.

European Search Report dated Dec. 20, 2007 for Application No. 07253220.

Examination Report dated May 13, 2008 for Application No. EP 07250402.0.

European Examination Report dated Mar. 19, 2009 for Application No. 07250926.

European Search Report dated Apr. 3, 2009 for Application No. 08252518.

European Search Report dated Apr. 3, 2009 for Application No. 08252524.

International Search Report dated Dec. 18, 2008 for Application No. PCT/US2008/058627.

Supplemental European Search Report dated Dec. 16, 2009 for Application No. EP06789155.

International Search Report dated Sep. 27, 2007 for Application No. PCT/US06/30022.

Patentability Report and Written Opinion dated Feb. 5, 2008 for Application No. PCT/US2006/030022.

Written Opinion dated Apr. 26, 2010 for Application No. EP 08252524.

U.S. Appl. No. 12/959,506, filed Dec. 3, 2010, Hibner et al.

* cited by examiner

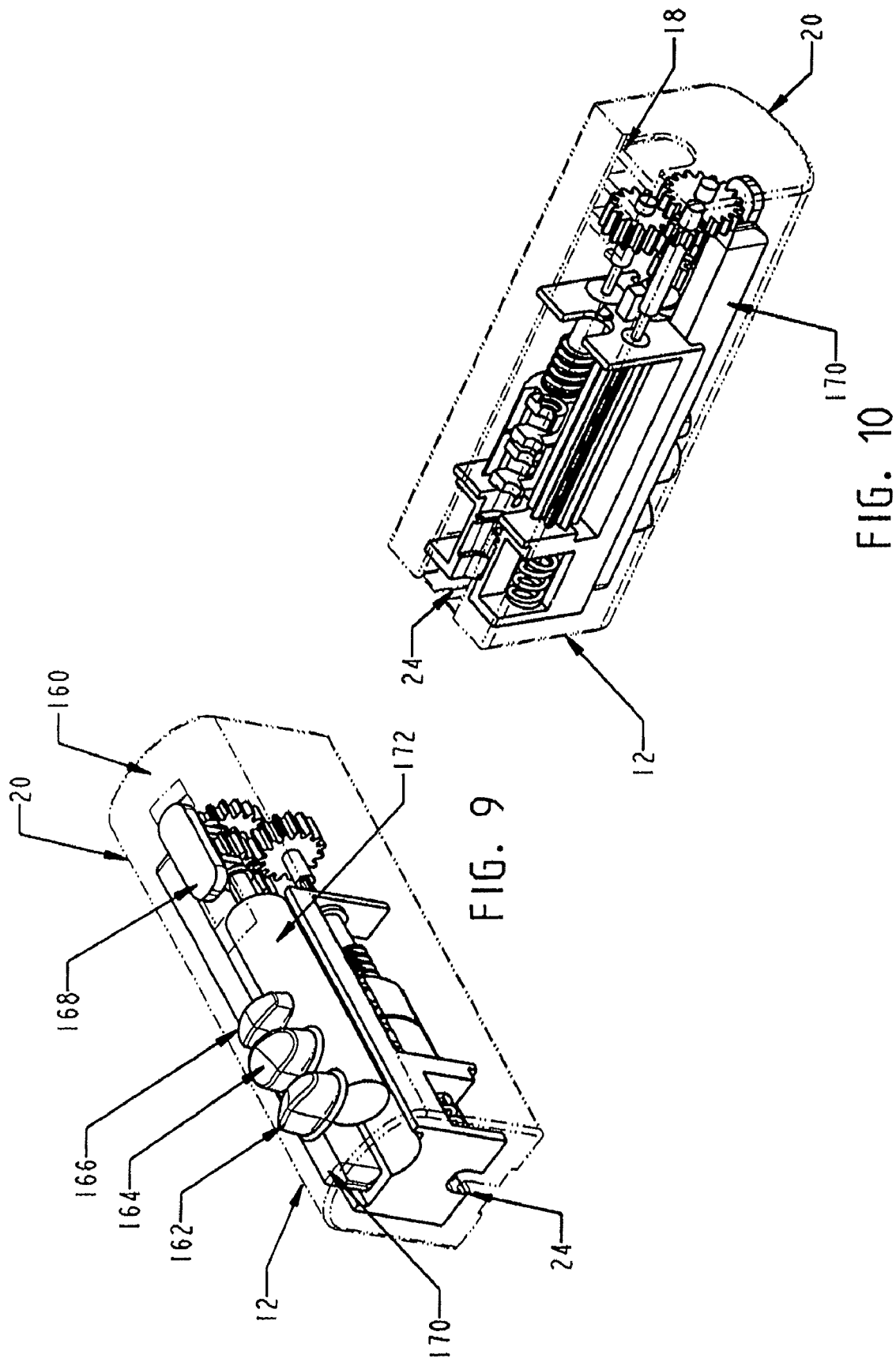

BIOPSY DEVICE WITH TRANSLATING VALVE MECHANISM

CROSS REFERENCE TO RELATED APPLICATIONS

This application is a continuation of the commonly-owned U.S. patent application Ser. No. 11/344,879 "BIOPSY DEVICE WITH REPLACEABLE PROBE INCORPORATING STATIC VACUUM SOURCE DUAL VALVE SAMPLE STACKING RETRIEVAL AND SALINE FLUSH" to Hibner, filed 1 Feb. 2006 now U.S. Pat. No. 7,662,109, the disclosure of which is hereby incorporated by reference in its entirety.

This application is also a continuation-in-part of the co-pending and commonly-owned U.S. patent application Ser. No. 11/198,558 "BIOPSY DEVICE WITH REPLACEABLE PROBE AND INCORPORATING VIBRATION INSERTION ASSIST AND STATIC VACUUM SOURCE SAMPLE STACKING RETRIEVAL" to Hibner et al., filed 5 Aug. 2005, the disclosure of which is hereby incorporated by reference in its entirety.

FIELD OF THE INVENTION

The present invention relates in general to biopsy devices, and more particularly to biopsy devices having a cutter for severing tissue, and even more particularly to biopsy devices for multiple sampling with a probe remaining inserted.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the tradename MAMMOTOME is commercially available from ETHICON ENDO-SURGERY, INC. for use in obtaining breast biopsy samples. These devices generally retrieve multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned patent applications: U.S. patent application Ser. No. 10/676,944, "Biopsy Instrument with Internal Specimen Collection Mechanism" filed Sep. 30, 2003 in the name of Hibner et al.; and U.S. patent application Ser. No. 10/732,843, "Biopsy Device with Sample Tube" filed Dec. 10, 2003 in the name of Cicenas et al. The cutter is cycled across the side aperture, reducing the sample time. Several alternative specimen collection mechanisms are described that draw samples through the cutter tube, all of which allow for taking multiple samples without removing the probe from the breast.

Even given the many advantages of such multiple sample taking core biopsy devices, in certain applications some surgeons continue to use less expensive biopsy devices guided in real time by an ultrasonic system. These simple biopsy systems omit a full function control console that operates the cutter and vacuum assistance. Instead, a manually controlled hand piece advances a cutter by either stored spring force, a constant pneumatic pressure source, or motor power. Then the surgeon activates a cutter motor to effect the tissue sample. Thus, the surgeon is challenged to maintain the biopsy probe at a desired surgical site while manipulating the patient's breast.

Spring-fired core needle biopsy devices rely upon a firing mechanism that thrusts forward a needle and a cutter to penetrate the tissue and to obtain a tissue sample rather than prolapsing tissue into a side aperture of a probe. Frequently, a surgeon may encounter an area of dense tissue that is more difficult to penetrate than the surrounding tissue during core needle biopsy. In particular, the lesion or tissue mass being targeted in the biopsy procedure may be difficult to penetrate, requiring the physician to push the biopsy needle with considerable force and/or speed in an attempt to penetrate the lesion and collect a sample.

When encountering such an area of dense tissue, it is common for surgeons using the type of firing core needle biopsy device described above to fire the device in order to penetrate the lesion and obtain a sample. However, due to the length of the firing stroke of such devices, which may be as long as 0.75 inches, it is nearly impossible for the surgeon to control the travel of the needle after firing. Consequently, the long needle stroke may cause uncertainty as to the needle tip location post fire. This may cause the surgeon to obtain a sample from the wrong area. In addition to missing the targeted tissue, long firing strokes may cause the needle to puncture the chest wall or pierce the skin, particularly when the targeted area is near the patient's chest wall. Even if the skin is not pierced, the long travel of the needle, along with the likelihood that the needle will be pushed off course by the force of the firing stroke, may lead to needlessly increased trauma for the patient. These spring-fired biopsy devices also yield a single sample per insertion, thus limiting the amount of diagnostic and therapeutic treatment that may be achieved without the increased discomfort and tissue trauma from repeated insertions. Based on surgeons' use of the long firing stroke feature of current devices to aid in penetrating tissue lesions, it is clear that the medical community sees the benefit of firing assistance when inserting a probe to the desired location.

In commonly-owned and co-pending U.S. patent application Ser. No. 11/035,873, BIOPSY INSTRUMENT WITH IMPROVED NEEDLE PENETRATION to Beckman, et al., filed on Jan. 10, 2005, the disclosure of which is hereby incorporated by reference in its entirety, manual mechanisms are disclosed that impart small reciprocating motions to the probe of a core biopsy device to render assistance in penetrating tissue, yet cutting is performed after the probe is properly positioned, thus avoiding taking samples from the wrong location. Moreover, retraction of a cutter tube between severing samples allows for retrieval of multiple samples without having to reinsert the probe through the skin again. A control system that is tethered to a hand piece of this core biopsy system provides vacuum assistance and other motor control algorithms with numerous clinical and safety features incorporated. Generally, the core biopsy device portion of the system is disposable and the control system is reused.

While these multiple sample core biopsy instruments have numerous advantages, it is believed that the diagnostic and therapeutic opportunities of core biopsy procedures would be more widely used if an economical biopsy device without an elaborate control system existed which did not require the disposal of the entire core biopsy device.

SUMMARY OF THE INVENTION

The present invention addresses these and other problems of the prior art by providing a biopsy device that has a needle with a probe tube defining a cutter lumen, a sample aperture formed in the probe tube, a barrier defining a first fluid passage and a second fluid passage that both distally terminate at the sample aperture. A motorized mechanism axially translates a cutter tube within the probe tube across the sample aperture to sever tissue prolapsed therein to axially translate the cutter tube. One of the first and second fluid passages is defined within the cutter tube and the other is defined between an outer surface of the cutter tube and an inner surface of the probe tube. Advantageously, a flush valve assembly responds to a flush control and to the distally positioned cutter tube to couple either the first or second fluid passage to a fluid supply while the other is at a lower pressure so that the needle is flushed. Thereby, tissue debris or coagulated blood may be flushed so that repeated tissue samples may be taken without impediment. However, the saline flush is selectively employed at the user's discretion, providing an economical reduction in the usage of saline and a corresponding reduction in the overall size of the fluid collection reservoir. It is also believed that certain pathology analyses would benefit from not subjecting tissue samples to a saline flush.

In another aspect of the invention, a core biopsy device has a probe assembly with a probe support structure that holds a probe having a side aperture. A cutter tube is slidingly received by the probe and sized to translate across the side aperture to sever prolapsed tissue. A hand piece includes a hand piece support structure having a lateral engaging portion that receives the probe assembly. Thereby, an economical incorporation of a replaceable probe and cutter tube into a laterally mounted assembly allows reuse of a powered hand piece, yet also provides an advantageous saline flush capability of the probe assembly.

In yet another aspect of the invention, a hand piece of a biopsy device has a proximal carriage that is also translated by the lead screw. The proximal carriage selectively actuates, when the distal carriage is distally positioned, a flush valve assembly contained in a probe assembly. A needle of the probe assembly has a cutter lumen for a cutter tube as well as a lateral lumen, both communicating with a side aperture in a probe tube. The same hand piece may instead be engaged to another probe assembly that utilizes the second carriage to actuate a tissue sample retraction mechanism.

In yet a further aspect of the invention, a biopsy system includes a hand-held device that is connected to a static vacuum source and to a fluid supply. The hand-held device includes a housing that is gripped to position a core biopsy probe. Actuating user controls on the housing translates a motor driven cutter that translates within the core biopsy probe to sever tissue that is prolapsed into a sample opening. Vacuum assist valve assembly in the hand-held device responds to positioning of the motor driven cutter to communicate static vacuum pressure from the static vacuum source to prolapse the tissue. Advantageously, a user may select to couple a fluid supply to the core biopsy probe to dispel debris and coagulated blood.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

FIG. 9 is a left isometric view from above of the reusable hand piece of FIG. 1 with the handle housing shown in phantom to expose the dual carriages distally translated;

FIG. 10 is a right isometric view from below of the reusable hand piece of FIG. 9 with the handle housing shown in phantom;

DETAILED DESCRIPTION OF THE INVENTION

Figure 1:
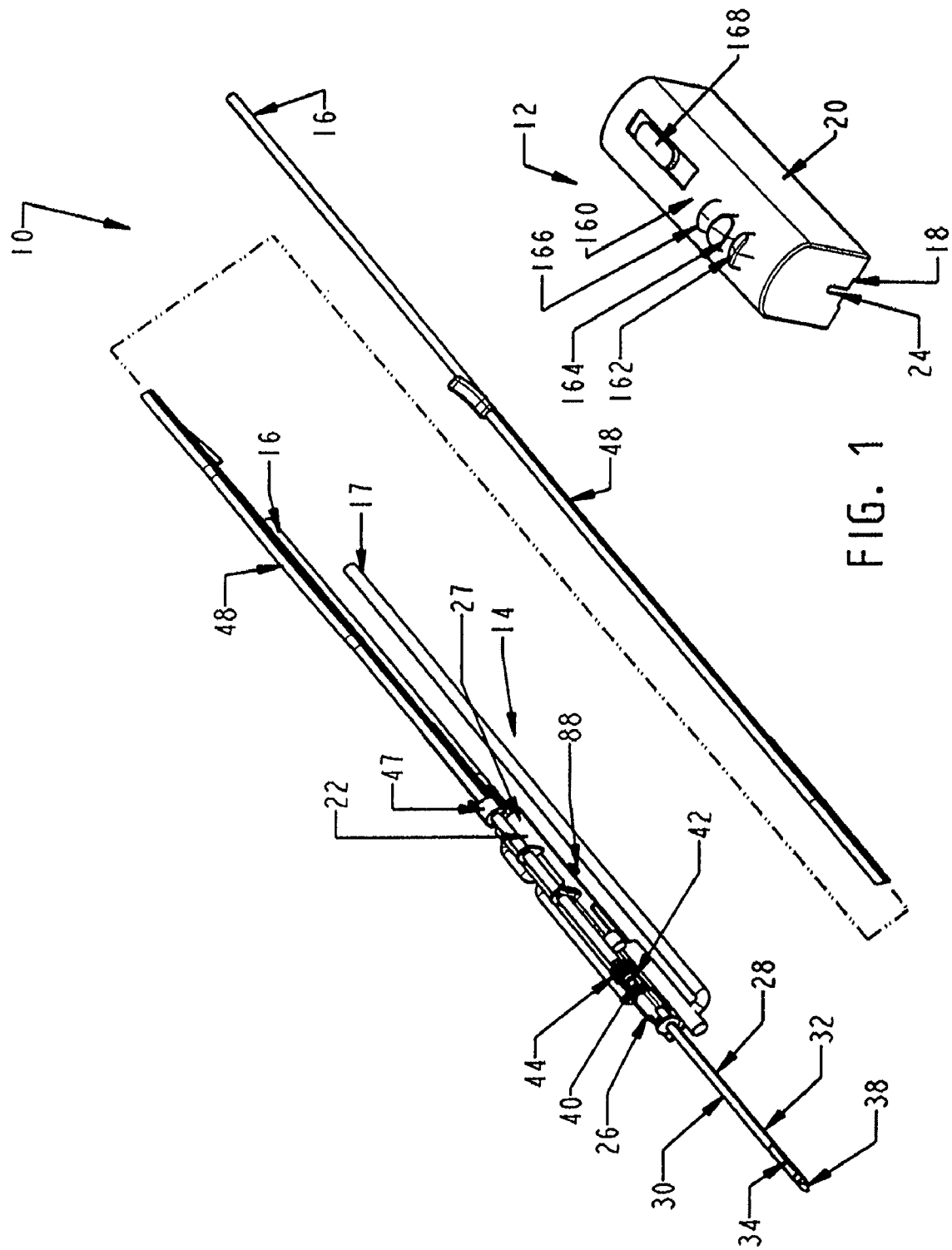
FIG. 1 is a left front isometric view from above of a biopsy device with a disposable probe assembly detached from a reusable hand piece.
Figure 2:
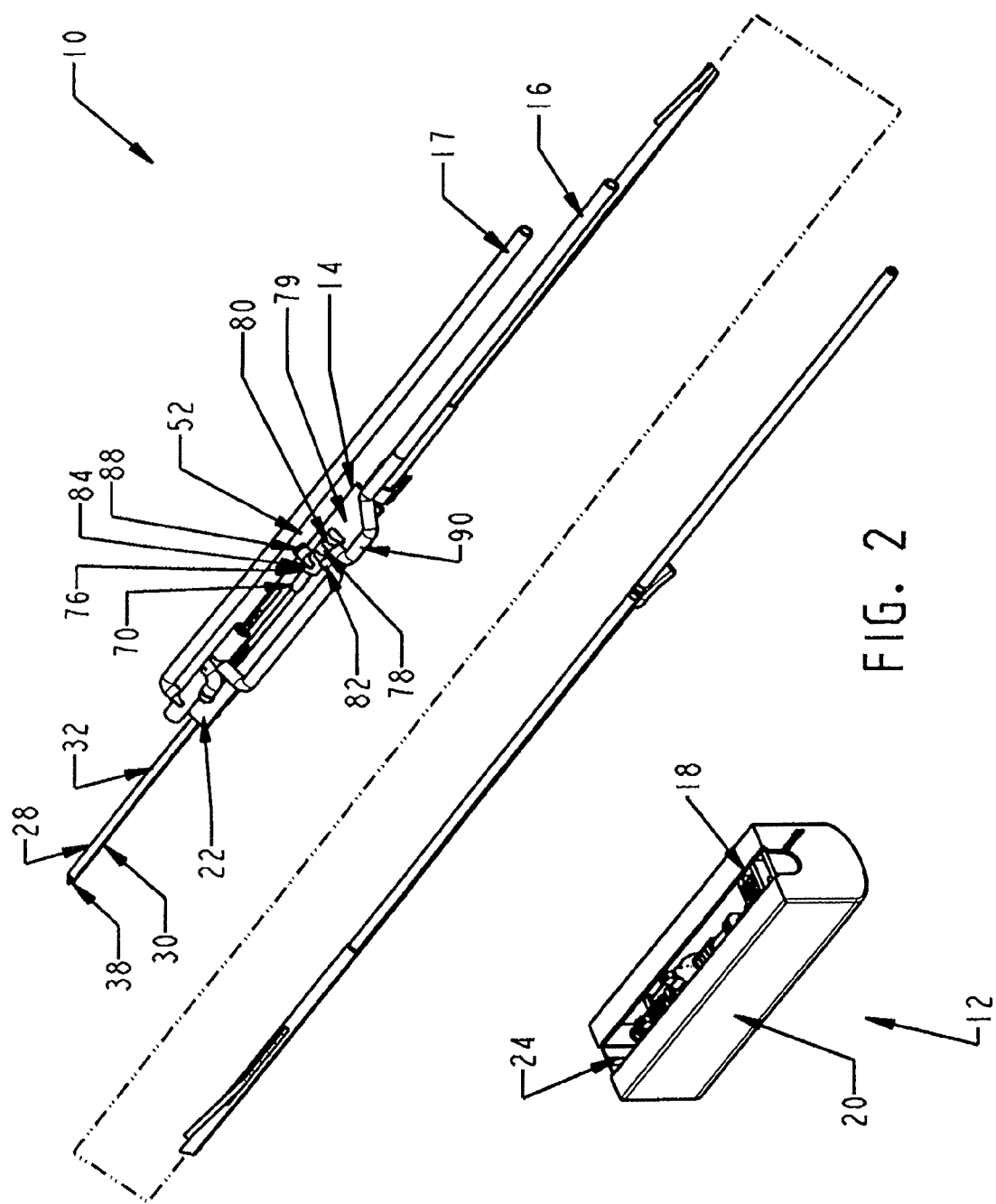
FIG. 2 is a right aft isometric view from below of the biopsy device of FIG. 1.

In FIGS. 1-2, a biopsy device 10 has a reusable hand piece 12 and a disposable probe 14 that enables economical taking of multiple percutaneous core biopsy samples by accessing a standard medical vacuum pump or wall-mounted vacuum access port (not shown) through an interfacing vacuum conduit 16. In addition, the biopsy device 10 advantageously incorporates a saline flush capability received from saline supply conduit 17. In the illustrative version, the reusable hand piece 12 is self-powered and suitable for use in conjunction with ultrasonic diagnostic imaging. The disposable probe 14 reduces the portion of biopsy device 10 that requires protective packaging to avoid contact with sharp surfaces and to keep it sterile prior to use. Further economy is accomplished by reducing the portion of the biopsy device 10 that is disposed as medical waste between uses. Movable components of the disposable probe 14 are advantageously locked until mounted in an access trough 18 formed in a handle housing 20 of the reusable hand piece 12. It should be appreciated that one or more standard mechanical, pneumatic, or electrical latches (not shown) may be integrated into the biopsy device 10 to secure the disposable probe 14 to the reusable hand piece 12.

In FIGS. 1-4, the disposable probe assembly 14 includes a substantially rectangular cover 22 sized to close the access trough recess 18 (FIGS. 1-2). An end slot 24 formed in the cover 20 (FIGS. 1-2, 5-6) is closed by a probe union sleeve 26 attached to an inner surface 27 (FIG. 1) of the substantially rectangular cover 22. A core biopsy needle ("probe") assembly 28 passes longitudinally through the probe union sleeve 26 and is formed by a probe tube 30 that includes an underlying lateral (vacuum) lumen 32 that communicates with a side aperture 34 (FIG. 1) via holes 35 (FIG. 4) near a distal opening 36 of the probe tube 30 that is closed by a piercing tip 38. A cutter tube 40 is sized to closely fit and translate within an inner diameter (i.e., cutter lumen) of the probe tube 30 with a length sufficient to close the side aperture 34 with a proximal end 42 extending from the probe union sleeve 26 to attach to a cutter gear 44, as depicted in FIG. 1.

It should be appreciated that the probe tube defines first and second fluid passages that are separated longitudinally within the probe tube and distally communicate with each other at the side aperture 34. In the illustrative version, the first fluid passage is defined within the cutter tube 40 and the second fluid passage is defined within the lateral lumen 32 that is "hard walled" apart from a cylindrical portion of the cutter lumen of the probe tube 35. However, for a cylindrical probe tube (not shown), a cutter tube may be axially offset within the cutter lumen of the probe tube such that the cutter tube may separate the first and second fluid passages, especially if the cutter tube need not be retracted for retraction of samples (e.g., vacuum retraction, straw retraction, single sample per insertion devices).

Figure 3:
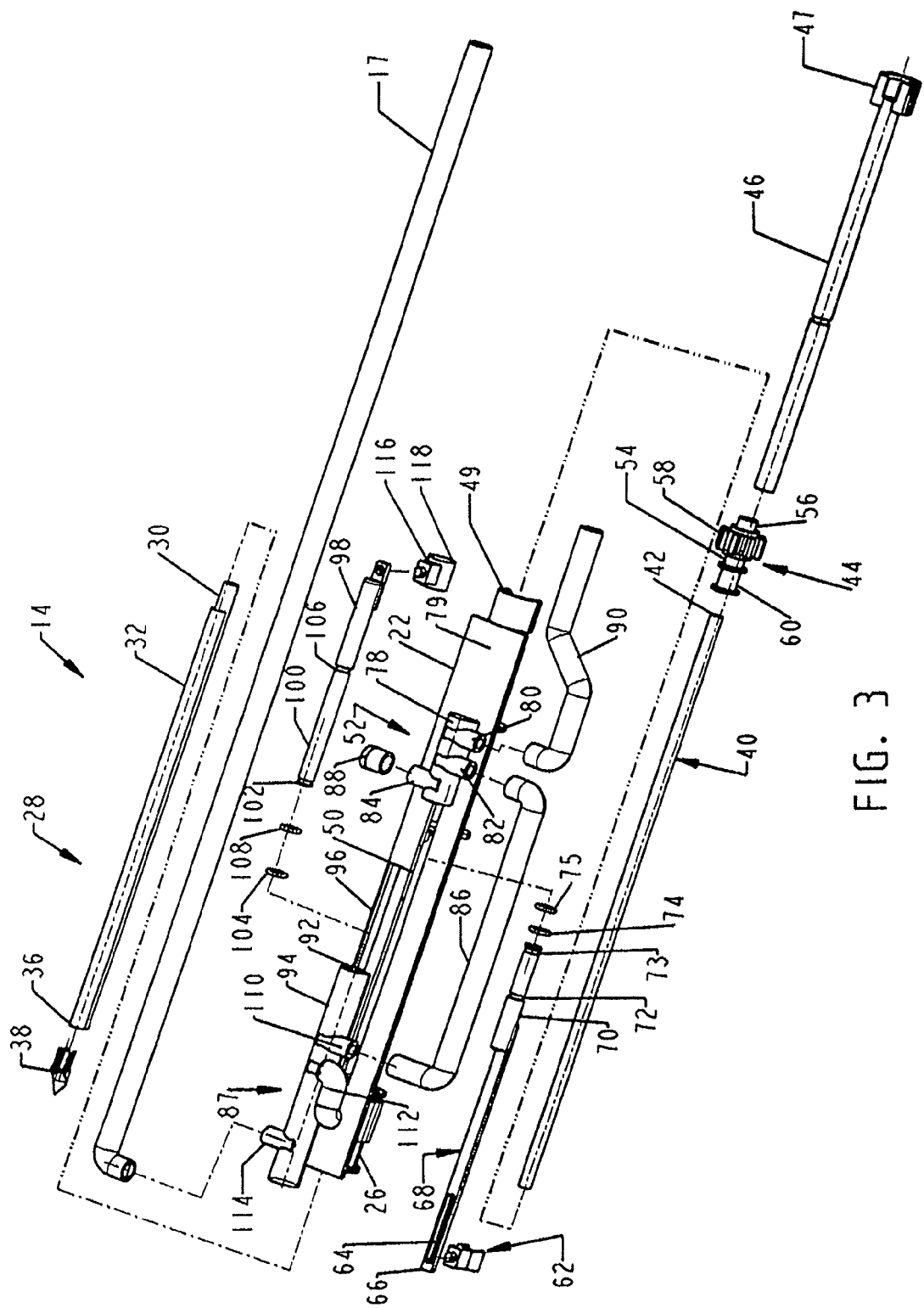
FIG. 3 is a right isometric view from below the disposable probe assembly of FIG. 1 disassembled to depict components of a vacuum assistance valve assembly and a saline flush valve assembly.
Figure 4:
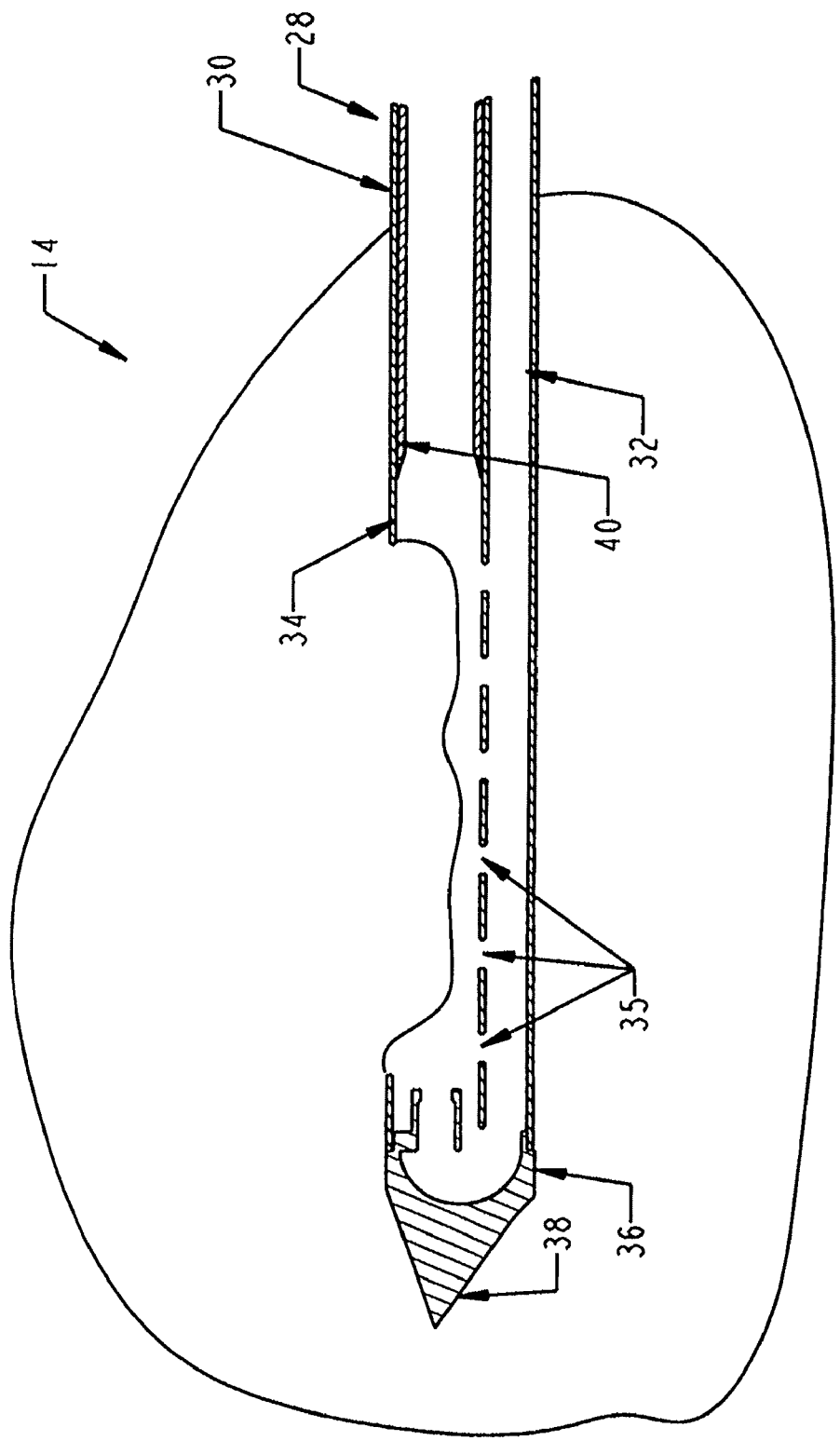
FIG. 4 is a longitudinal, vertical cross sectional view through a probe of the disposable probe assembly of FIG. 1.

With particular reference to FIG. 3, sample retrieval tube 46 is received within a proximal opening in the cutter gear 44 and in turn proximally terminates itself at a half cylinder connector 47 positioned proximate to a rear support bracket 49 attached to the generally rectangular cover 22. As described in the cross referenced application Ser. No. 11/198, 558, the half cylinder connector 47 attaches to a moving portion of a sample holding apparatus and the rear support bracket 49 attaches to a stationary portion of the sample holding apparatus (proximal sample stacker 48). The relative movement increments a capture mechanism as samples are proximally stacked with vacuum being ported through the half cylinder connector 47 and sample retrieval tube 46 to extract samples from the cutter tube 40.

With continued reference to FIG. 3, proximal to the probe union sleeve 26 is an elongate slot 50 that is part of a vacuum assist valve assembly 52. The cutter gear 44 includes distal and proximal annular recesses 54, 56 flanking spur gear teeth 58 that engage the reusable hand piece 12 as described below. A more distal annular recess 60 is gripped by a first valve post 62 that is engaged to longitudinally translate in an elongate post slot 64 of a distal portion 66 of a vacuum valve actuator 68.

Figure 5:
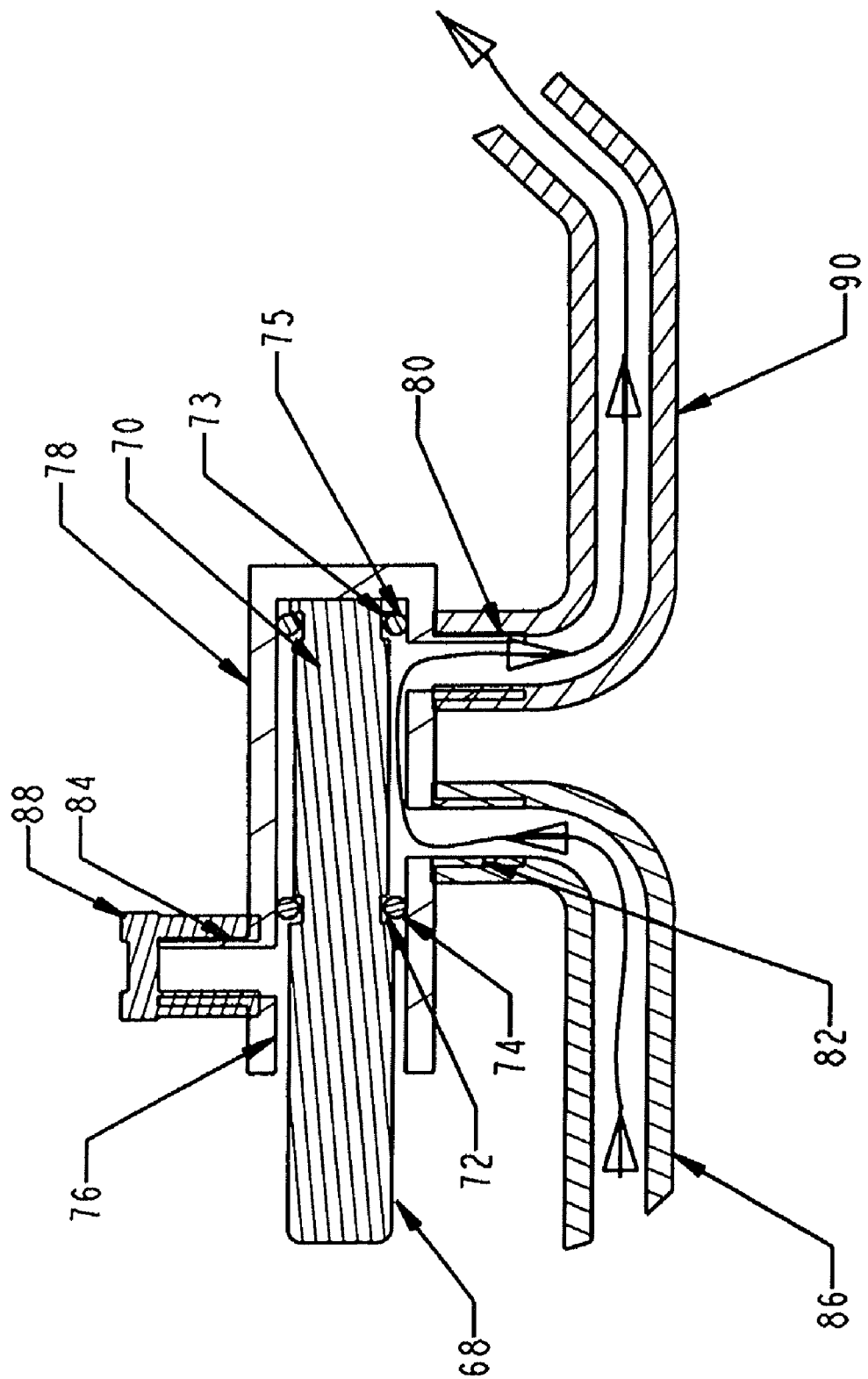
FIG. 5 is a longitudinal, horizontal cross sectional view through a vacuum assist valve assembly in an initial state (i.e., communicating supply vacuum to the probe to prolapse tissue) of the disposable probe assembly of FIG. 1.

In FIGS. 3, 5, a cylindrical proximal portion 70 of the vacuum valve actuator 68 has distal and proximal O-ring grooves 72, 73 that respectively retain distal and proximal dynamic O-ring seals 74, 75 that move within a distally open cylindrical valve bore 76 of a vacuum valve body 78 molded onto an outer surface 79 of the substantially rectangular cover 22.

Figure 6:
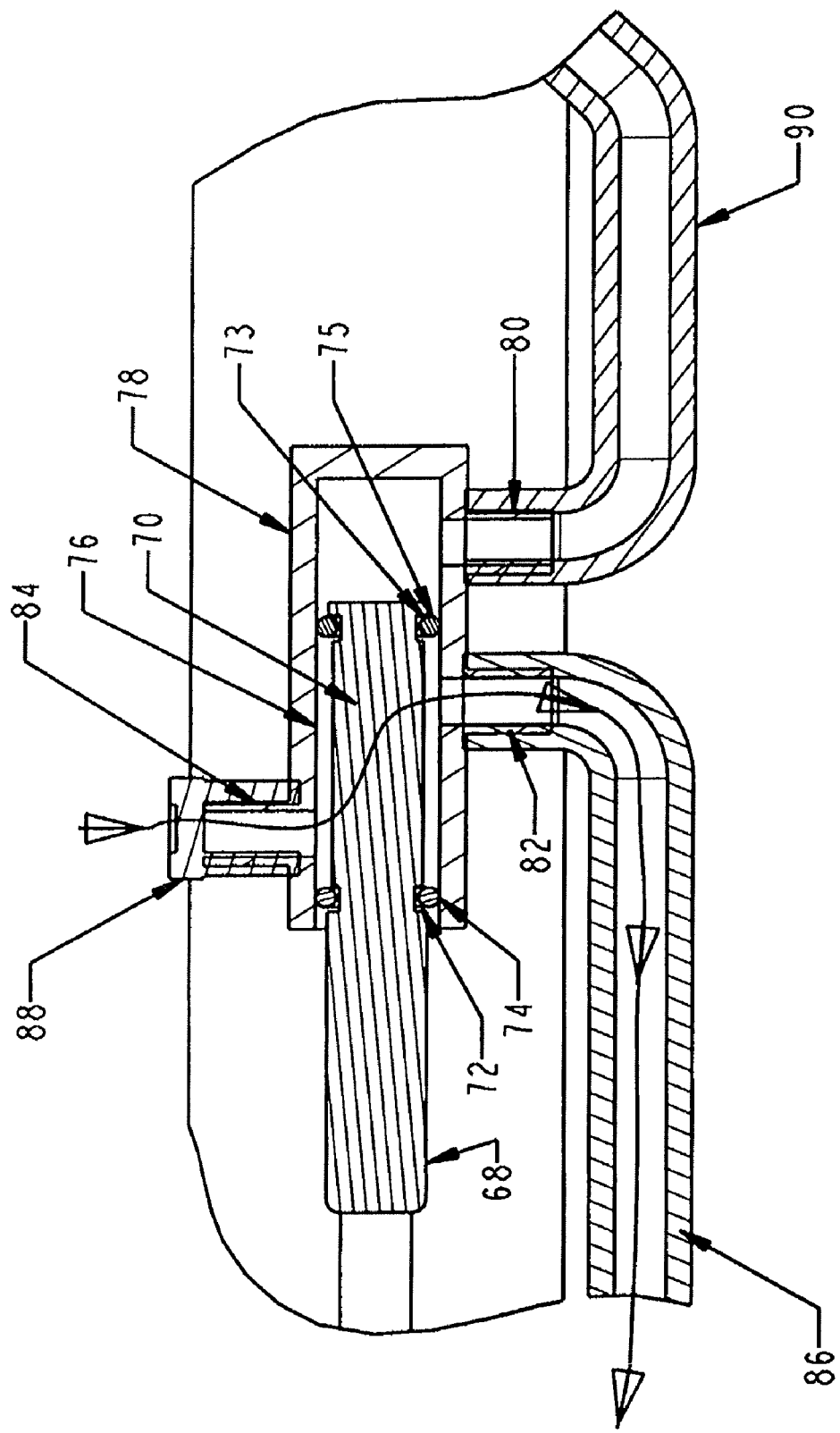
FIG. 6 a longitudinal, horizontal cross sectional view through the vacuum assist valve assembly in a distally translated state (i.e., communicating increased pressure such as atmospheric pressure to the probe) of the disposable probe assembly of FIG. 1.

In an initial state depicted in FIG. 5, the vacuum valve actuator 68 is in a retracted position (along with the cutter tube 40), allowing communication between a proximal vacuum port 80 and a center vacuum port 82. In FIG. 6, distal translation of the vacuum valve actuator 68 enables communication between the center vacuum port 82 and a distal vacuum port 84. The center vacuum port 82 is attached to a proximal end of a distal vacuum conduit 86 whose other distal end is connected through the rectangular cover 22 to the probe union sleeve 26 (FIGS. 2-3). It should be appreciated that the probe union sleeve 26 includes fluidic passages that communicate between the proximal end of the vacuum lumen 32 and the distal vacuum conduit 86 as allowed by the saline flush valve assembly 87 (FIG. 7).

Returning to the vacuum assist valve assembly 52 of FIGS. 2-3, 5-6, the distal vacuum port 84 is attached to a hose nib 88 that is exposed to atmospheric pressure. Hose nib 88 may include an air and/or saline filter. Alternatively, hose nib 88 may be connected to a positive pressure source (e.g., fluid pump) or a negative pressure source (e.g., vacuum pump, syringe) to aspirate fluids. Likewise, hose nib 88 may be used to lavage the tissue cavity with saline, pain medication, or bleeding control fluids. The proximal vacuum port 80 communicates through a proximal vacuum conduit 90 to the interfacing vacuum conduit 16.

In FIGS. 2-3, 7-8, the flush valve assembly 87 includes a proximally open saline valve bore 92 formed in a saline valve body 94 molded onto the outer surface 79 of the substantially rectangular cover 22 distal to a laterally offset longitudinal slot 96 (FIG. 3) defined in a distal portion of the substantially rectangular cover 22.

Figure 7:
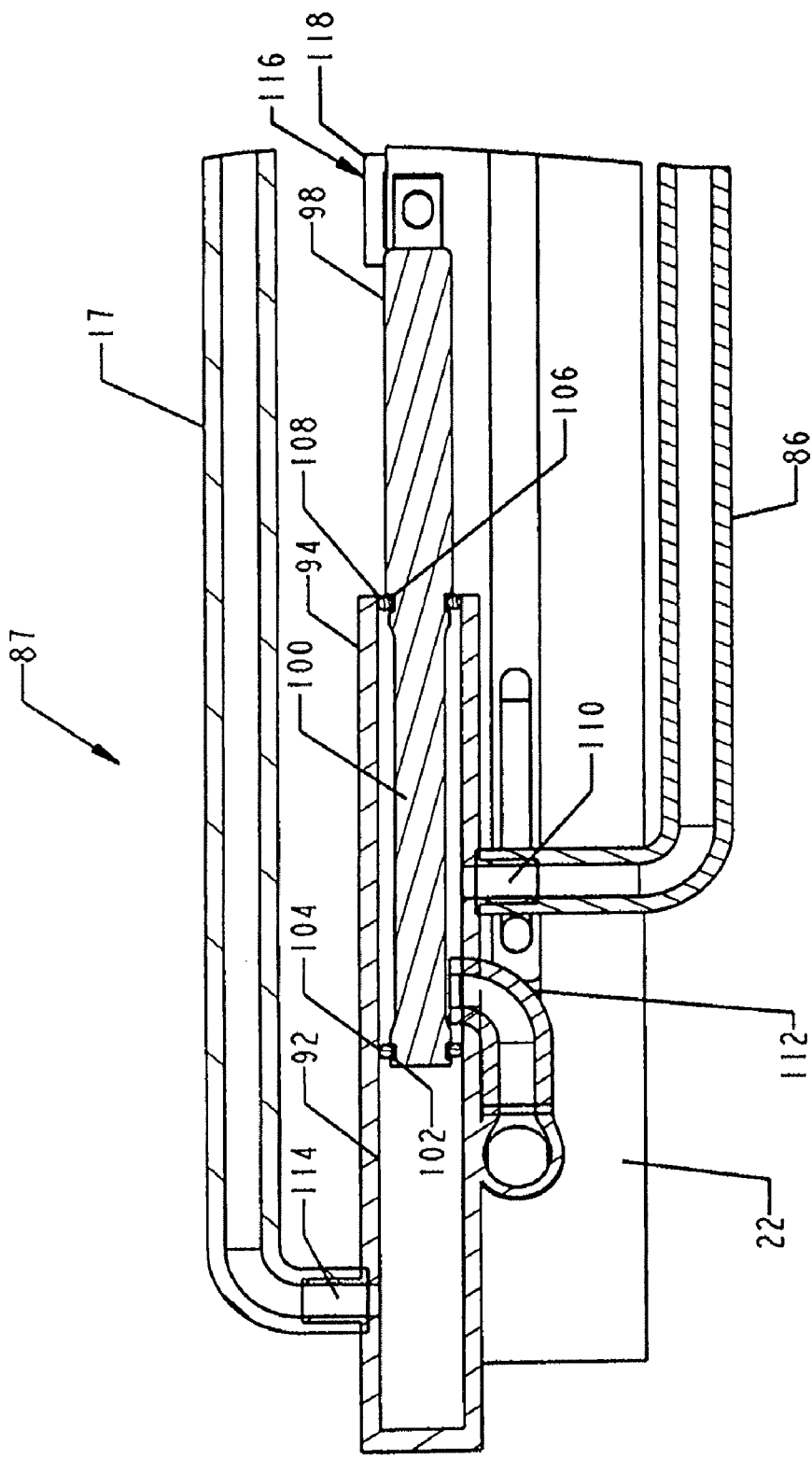
FIG. 7 is a longitudinal, horizontal cross sectional view viewed from below through a saline flush valve assembly in an initial, retracted state (i.e., communication allowed between center port of the vacuum assist valve assembly and the probe) of the disposable probe assembly of FIG. 1.
Figure 8:
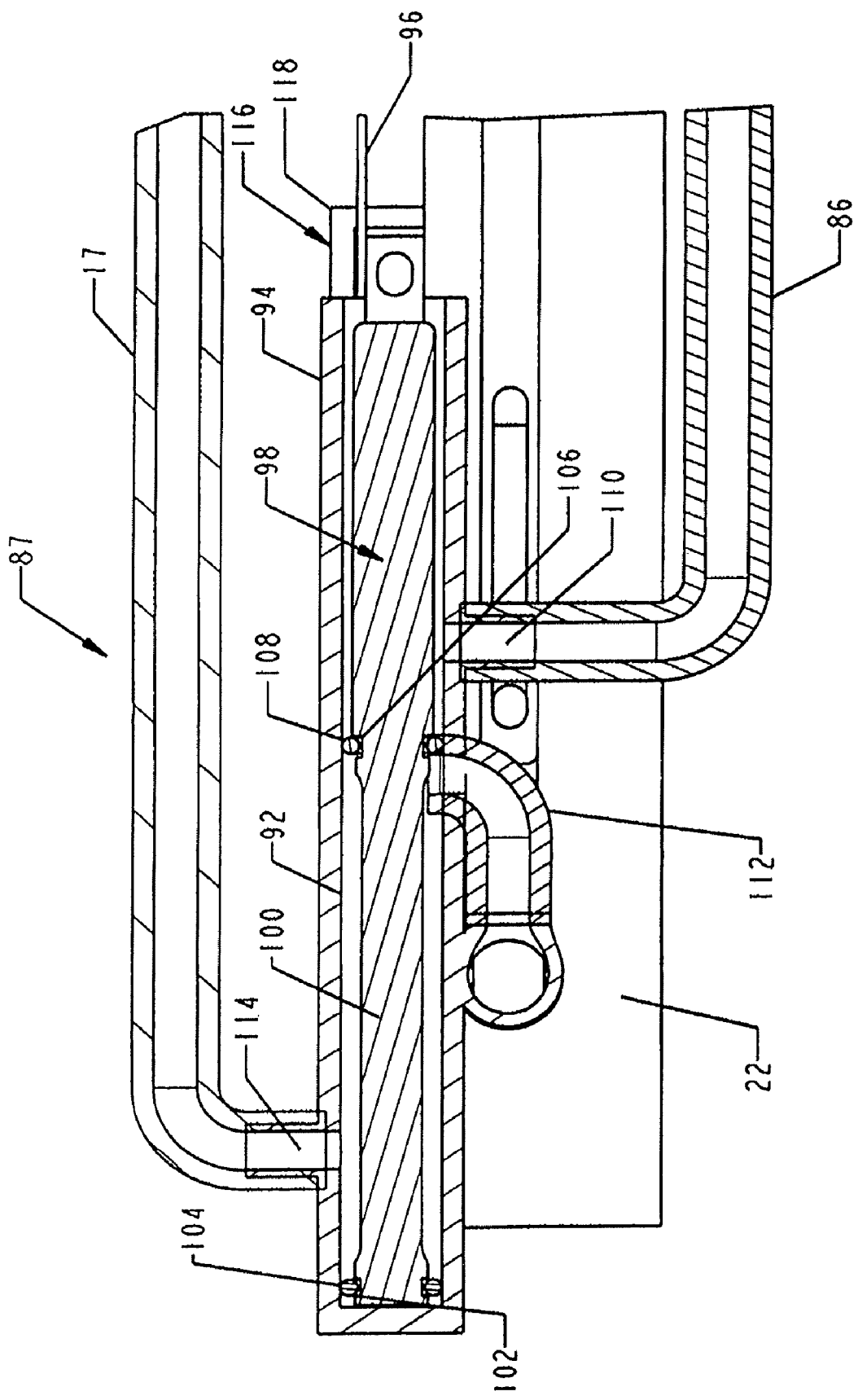
FIG. 8 is a longitudinal, horizontal cross sectional view viewed from below through the saline flush valve assembly in a distally translated state (i.e., communication allowed between a saline supply conduit and the probe) of the disposable probe assembly of FIG. 1.

With particular reference to FIGS. 3, 7, a saline valve actuator 98 includes a distal cylindrical spool 100 that is sized to be slidingly received within the proximally open saline valve bore 92. A distal O-ring groove 102 that receives a distal saline O-ring 104 and a mid-shaft O-ring groove 106 that receives a mid-shaft saline O-ring 108 are spaced on the distal cylindrical spool 100 to selectively allow communication between a proximal saline port 110, which is attached to the distal end of the distal vacuum conduit 86, and a center molded conduit 112 that communicates through the probe sleeve union 26 to the vacuum lumen 32 when the saline valve actuator 98 is proximally positioned, as depicted in FIG. 7. When the saline valve actuator 98 is distally positioned, as depicted in FIG. 8, the center molded conduit 112 communicates with a distal saline port 114 that is attached to a proximal end of the saline supply conduit 17. A proximal end of the saline valve actuator 98 is attached to a saline slot link 116 that longitudinally slides within the laterally offset longitudinal slot 96 extending a proximal carriage engagement member 118 out of the inner surface 27 of the substantially rectangular cover 22.

Figure 11:
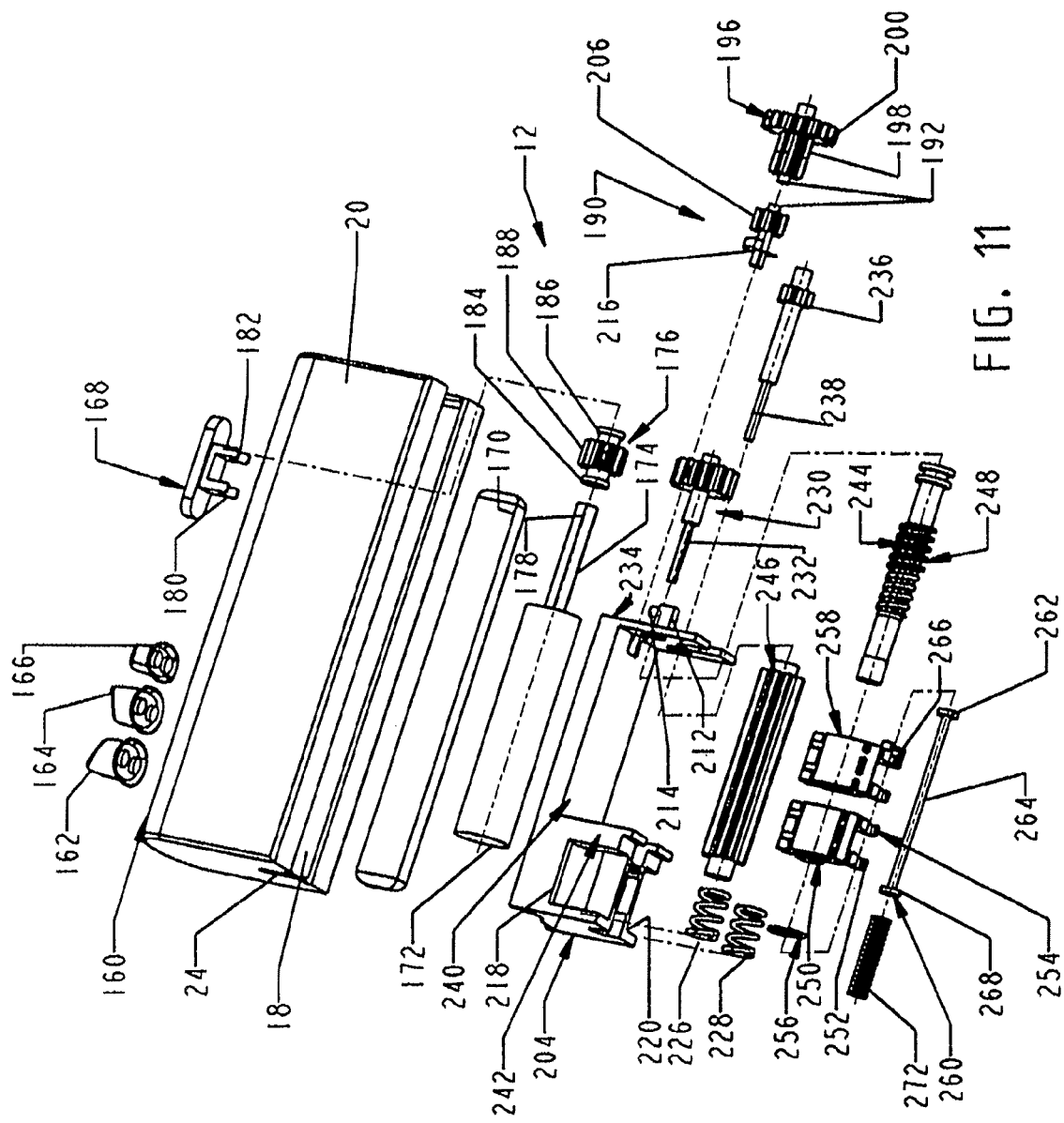
FIG. 11 is a left isometric exploded view from below of the reusable hand piece of FIG. 1.

With reference to FIGS. 1-2, 9-11, the reusable hand piece 12, as described in previously cross referenced U.S. patent application Ser. No. 11/198,558 includes four user controls aligned on a top surface 160 of the housing 20, specifically from most distal to most proximal: a forward motor rotation key 162, a reverse motor rotation key 164, a saline flush key 166 and a slide button 168 for selecting insertion mode or sample taking mode. The keys 162-166 control a control circuit 170, which may include integral power storage (e.g., batteries, fuel cell, etc.) for untethered use. With particular reference to FIG. 11, the forward motor rotation key 162 causes a DC motor 172 to rotate its motor output shaft 174 in a forward rotation. A slide spur gear 176 includes an internal keyed engagement with a longitudinal key groove 178 on the motor output shaft 174 that allows longitudinal positioning by the slide button 168. In particular, fore and aft brackets 180, 182 of the slide button 168 engage distal and aft annular grooves 184, 186 that flank spur gear teeth 188 of the slide spur gear 176.

Figure 12:
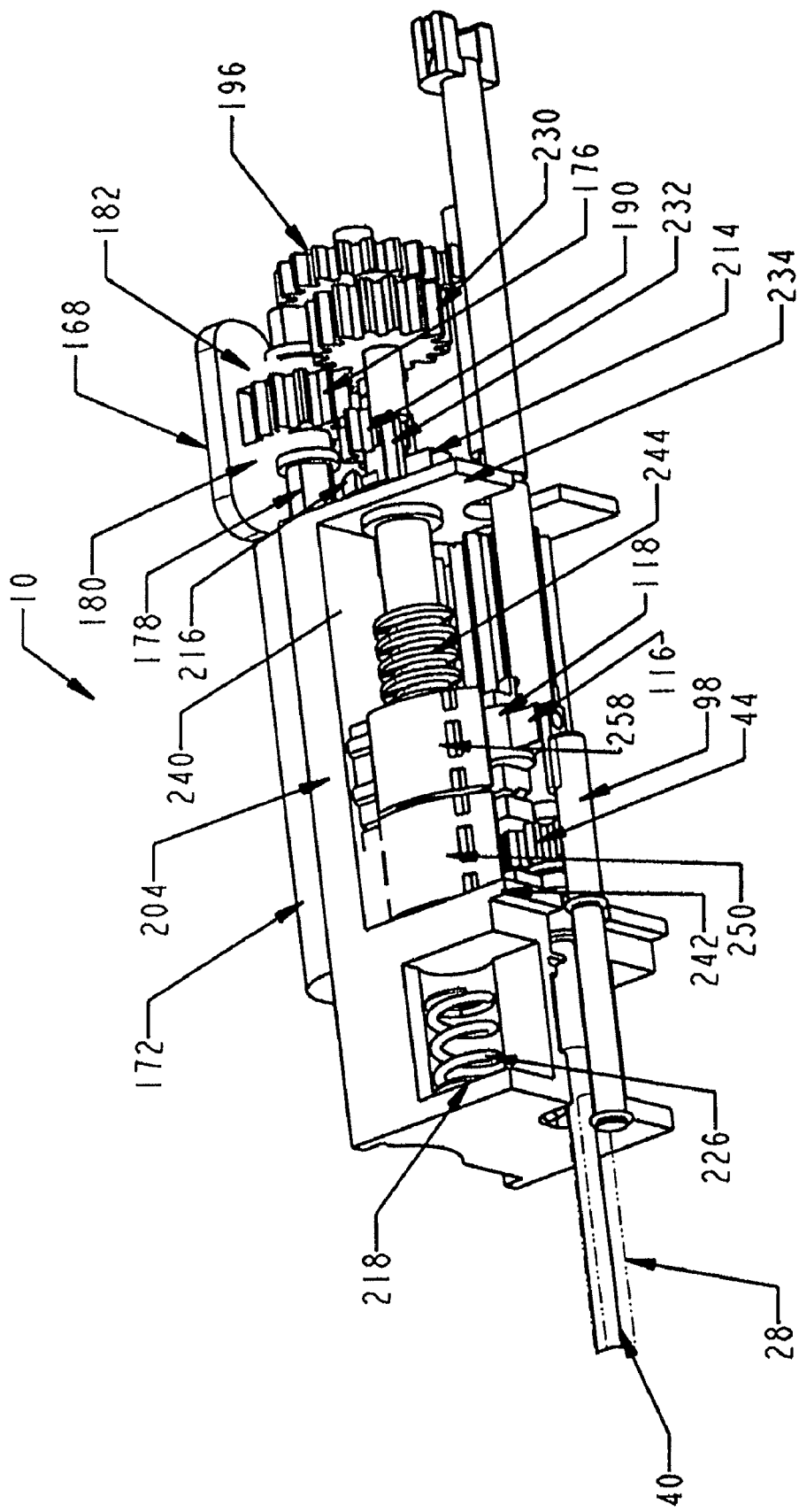
FIG. 12 is a left isometric view from slightly below the reusable hand piece with the handle housing removed to expose the distally positioned dual carriages and a portion of the disposable probe assembly installed with a generally rectangular cover removed.
Figure 13:
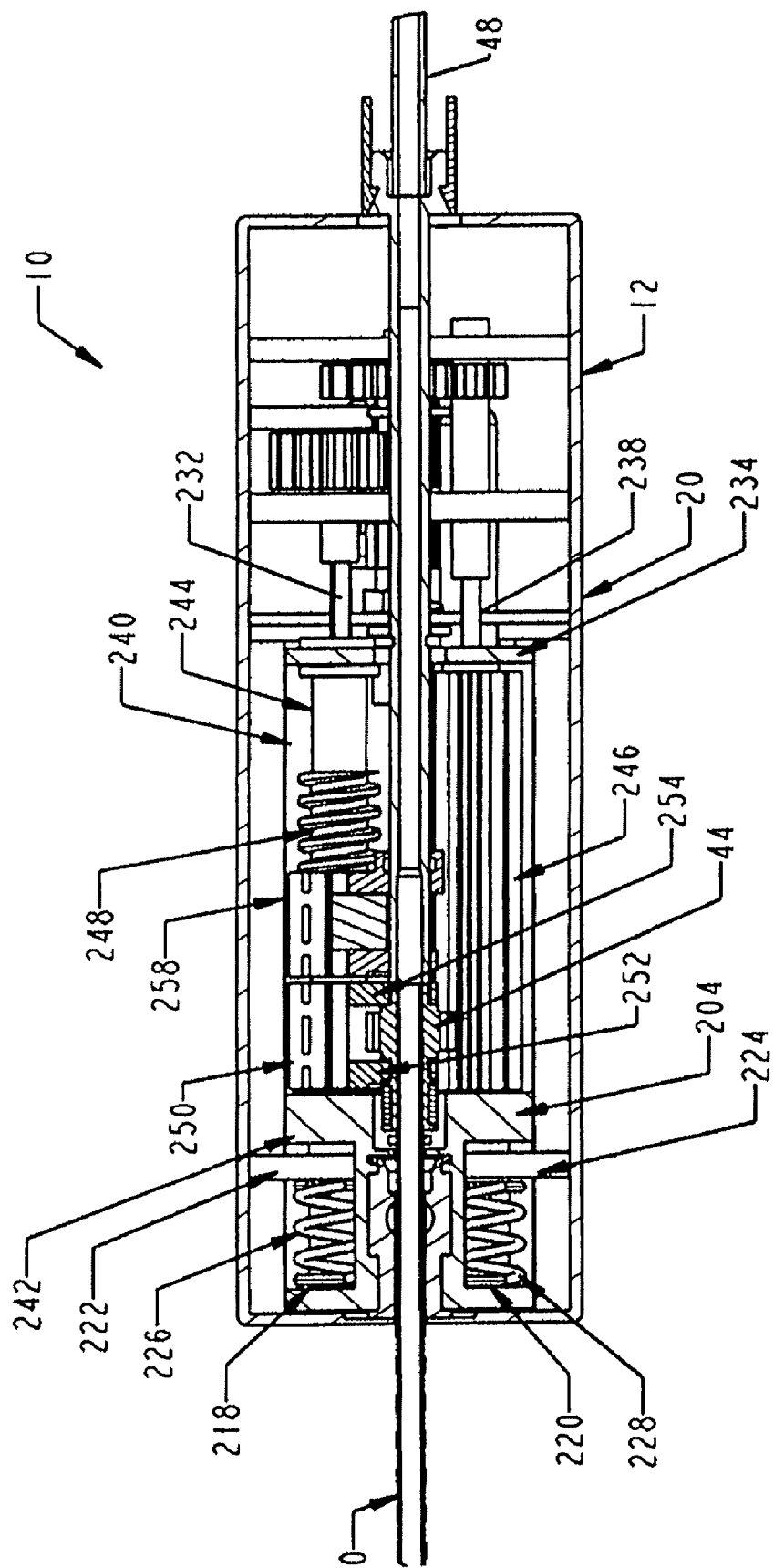
FIG. 13 is a bottom view taken along a horizontal cross section through the probe of an assembled biopsy device of FIG. 1 with dual carriages both distally positioned.

When the slide button 168 is moved distally, the slide spur gear 176 engages a tissue penetration gear 190 that spins on a common shaft centerline 192 forward of a gearbox input gear 196. Gearbox input gear 196 consists of a distal small gear 198 and a proximal large gear 200. The tissue penetration gear 190 has spur gear teeth 206 that engage the slide spur gear 176. A frame post 212 projects proximally from an aft wall 234 of a frame 204 with a strike pin 214 projecting upwardly from the frame post 212. In FIGS. 11-12, a circular cam wheel 216 is attached to a distal side of the tissue penetration gear 190. Rotating the tissue penetration gear 190 urges the strike pin 214, and thus the frame 204, proximally. In FIGS. 11, 13, left and right spring cavities 218, 220 (when viewed from above), formed longitudinally in distal corners of the frame 204, respectively receive inwardly projecting left and right tabs 222, 224 (FIG. 13) from the cover 20 and receive left and right compression springs 226, 228. In particular, a distal end of each compression spring 226, 228 presses against a distal inner surface of the respective spring cavity 218, 220. A proximal end of each compression spring 226, 288 is grounded against a respective tab 222, 224 of the cover 20. Thus, the frame 204 is biased distally within the cover 20. Movement of the frame 204 proximally compresses these compression springs 226, 228 that thereafter assert a restoring force.

When the slide button 168 is moved proximally, the slide spear gear 176 is moved into engagement with the gearbox input gear 196, specifically the distal small gear 198, which engages and turns a translation large input gear 230 whose shaft 232 passes through the aft wall 234 of the frame 204. The proximal large gear 200 of the gearbox input gear 196 engages and turns a rotation small input gear 236 whose shaft 238 passes through the aft wall 234. The frame 204 includes a carriage recess 240, defined between a partition 242 and the aft wall 234. The carriage recess 240 contains longitudinally aligned left side lead (translation) screw 244 and right-side rotation spur gear 246 that are attached for rotation respectively with the shafts 232, 238. The partition 242 is positioned aft of the left and right tabs 222, 224 of the cover 20 and also defines in part the left and right spring cavities 218, 220.

The rotation spur gear 246 engages the cutter gear 44 when the disposable probe 14 is inserted, imparting a rotation as the cutter tube 40 and cutter gear 44 translate longitudinally in response to the rotation of the lead (translation) screw 244. This translation is caused by lead screw threads 248. In particular, a distal carriage (cutter carriage) 250 is longitudinally moved on the lead screw threads 248. Distal and proximal J-hook extensions 252, 254 project downwardly from the distal carriage 250 to engage the distal and proximal annular recesses 54, 56 of the cutter gear 44 (FIG. 3). Distal of the distal carriage 250, a biasing spring 256 urges against the distal carriage 250, which assists in engagement of the lead screw threads 248 with the distal carriage 250.

Figure 14:
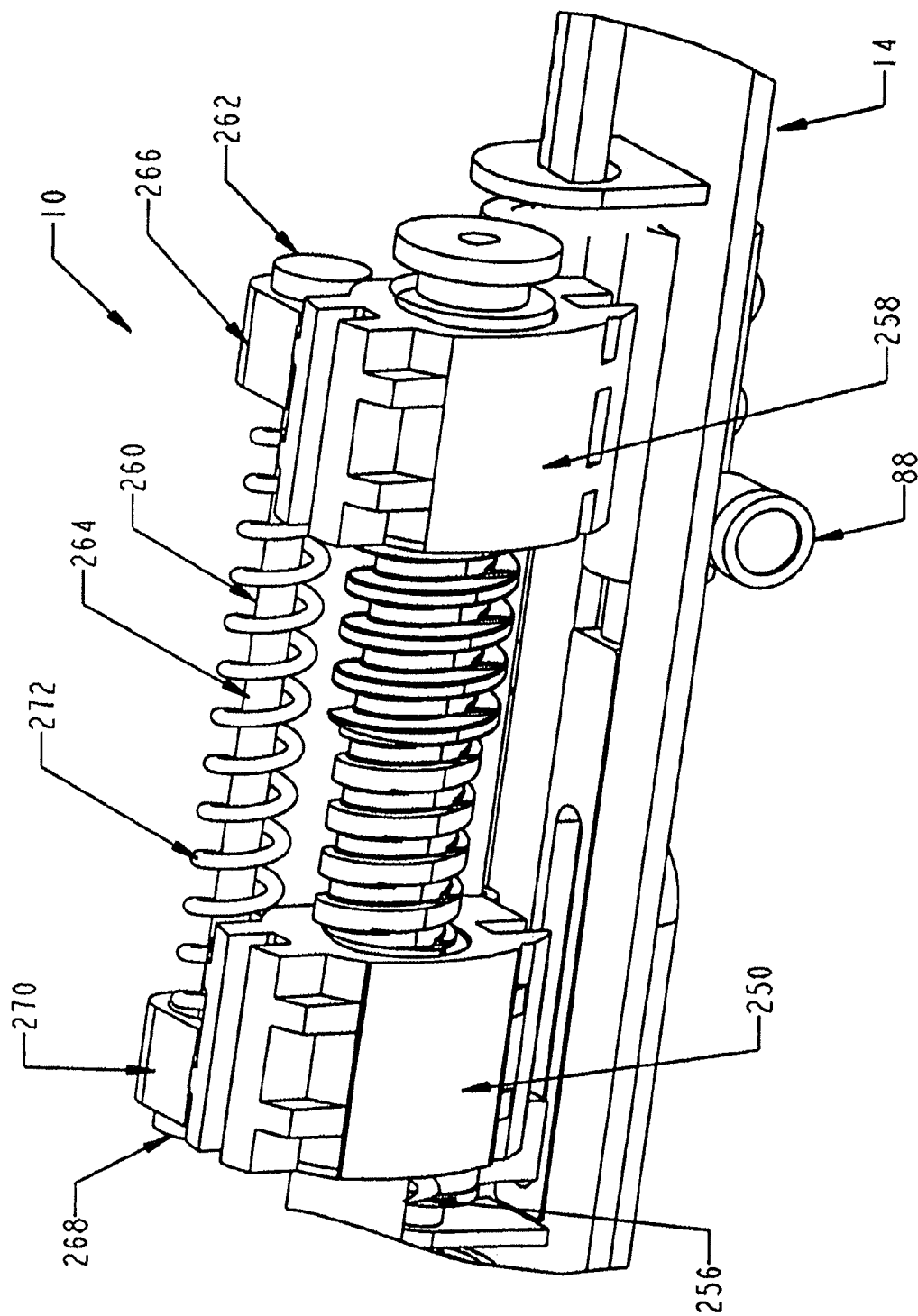
FIG. 14 is a left isometric detail view of the dual carriages in opposite translations as initially positioned during engagement of the disposable probe assembly and during insertion into tissue.
Figure 15:
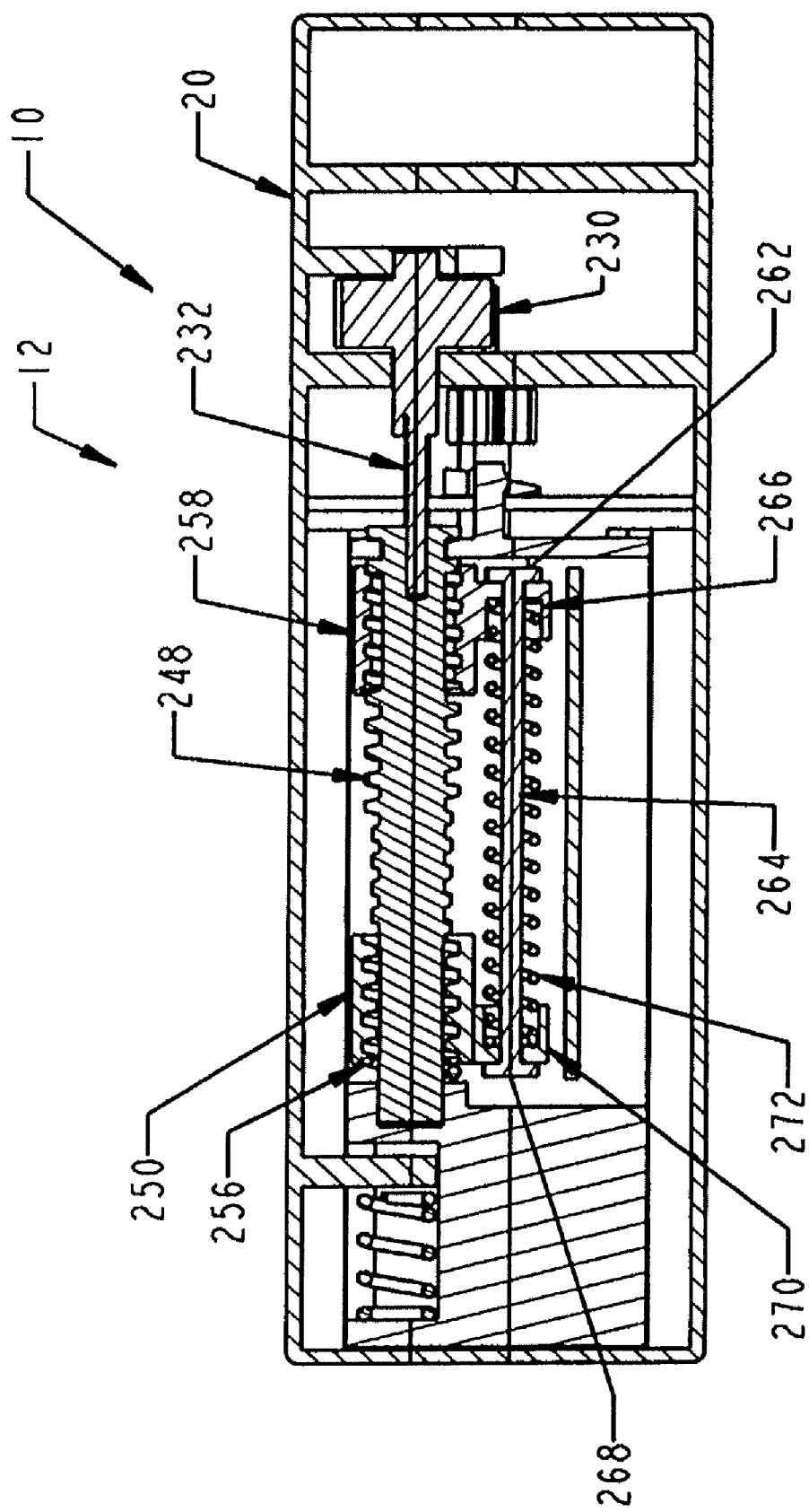
FIG. 15 is a bottom view taken in horizontal cross section through a lead screw of the reusable hand piece of FIG. 14.
Figure 16:
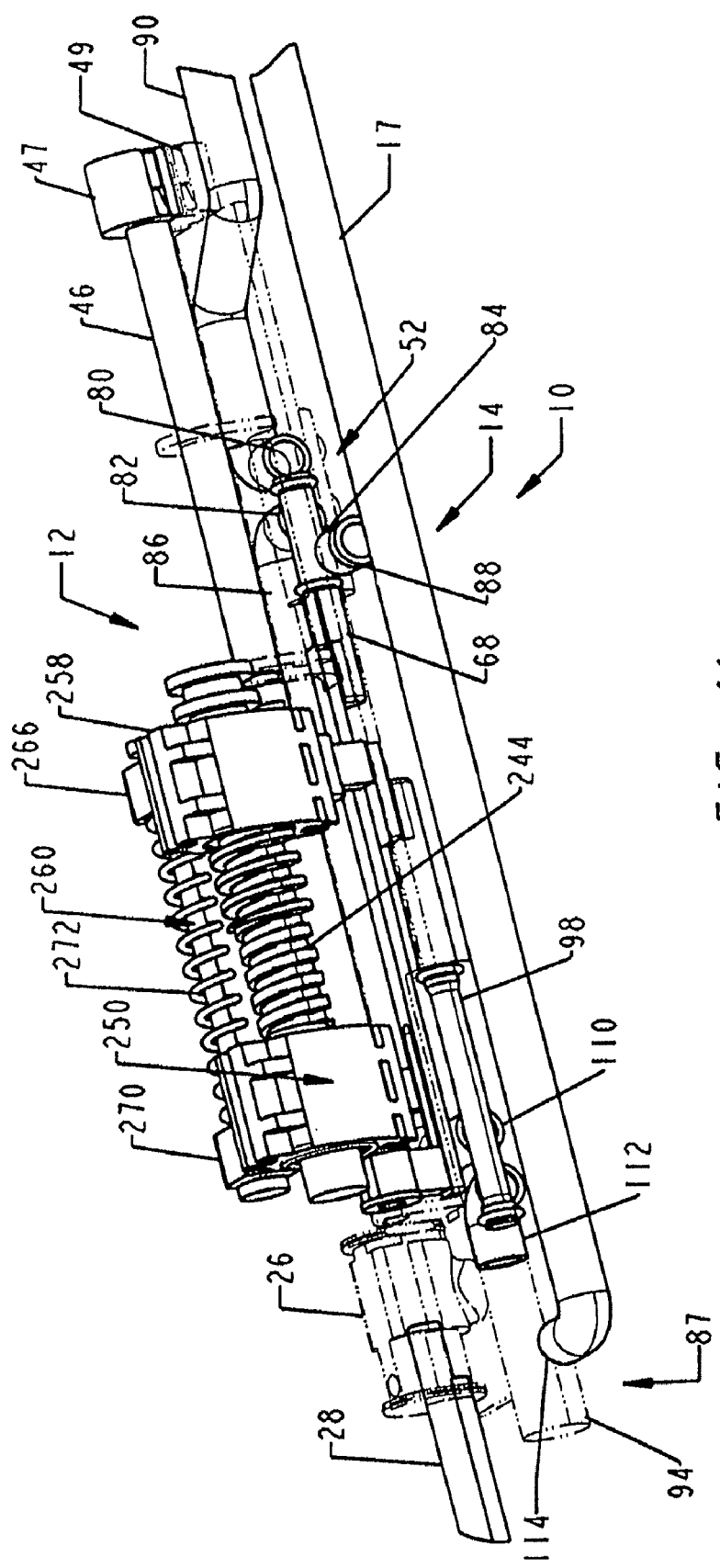
FIG. 16 is a left isometric view of portions of the biopsy device of FIG. 1 depicted to include the dual carriages in the initial position and sleeve union in phantom and also depicted with the probe and pneumatic components of the disposable probe assembly.

In FIGS. 11, 14-15, a sliding pin 260 has a proximal carriage sliding pin retainer 266 attached to a proximal carriage 258. A shaft 264 of the sliding pin 260 also passes through a distal carriage sliding pin retainer 270 attached to the distal carriage 250. Sliding pin 260 has a proximal end 262 and a distal end 268 to prevent the sliding pin 260 from disengaging from the carriage sliding pin retainers 266, 270. A sliding pin spring 272 resides on the sliding pin 260 and is constrained at each end by carriage sliding pin retainers 266, 270.

With the components of the reusable handpiece 12 now introduced, a sequence of use of the biopsy device 10 will be described. The disposable probe assembly 14 is installed into the reusable hand piece 12. In so doing, the distal carriage 250 engages the cutter gear 44 to position (translate) the cutter tube 40, initially in a distal position as depicted in FIG. 12. During installation, the proximal carriage 258 engages the proximal carriage engagement member 118 feature located on saline slot link 116 that engages the proximal portion of the saline valve actuator 98. A proximally stacking sample retrieving device 48 is attached to the disposable probe assembly 14 to provide a pneumatic vacuum bias to the cutter tube 40 and to hold retracted tissue samples.

With the biopsy device 10 assembled, the reusable handpiece 12 is manipulated to insert the piercing tip 38 of the core biopsy needle (probe) assembly 28 into tissue. Penetration of dense tissue is assisted by moving the slide button 168 distally to a "tissue insertion mode" wherein the slide spur gear 176 engages the tissue penetration gear 190. Depression of the forward motor rotation key 162 turns these gears 176, 190 causing the circular cam wheel 216 to turn against strike pin 214 that creates proximal longitudinal motion of frame 204 and the attached core biopsy needle (probe) assembly 28 of approximately 0.1 inch at a rotation rate of 7 cycles per second (FIG. 12). Left and right compression springs 226, 228 provide the restoring distal longitudinal motion to frame 204 and probe assembly 28 as left and right compression springs 226, 228 are repeatedly compressed between the distal surface of the left and right spring cavities 218, 220 of the frame 204 and the left and right tabs 222, 224 of the housing 20. The restoring distal longitudinal motion to frame 204 and core biopsy needle (probe) assembly 28 result in a corresponding distal motion of piecing tip 38 that assists in penetrating tissue.

Figure 17:
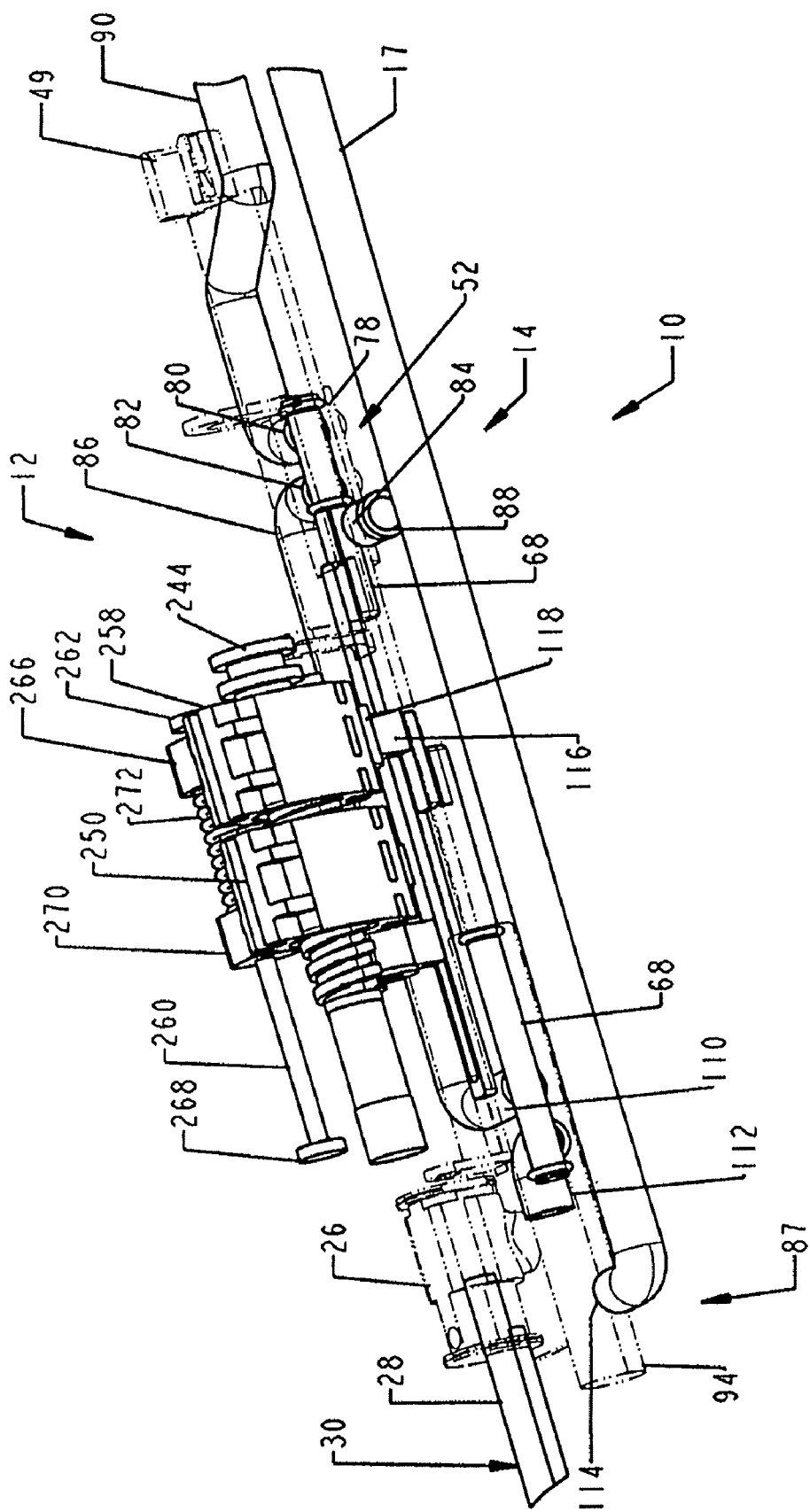
FIG. 17 is a left isometric view from below the portions of the biopsy device of FIG. 16 after retraction of the distal carriage.
Figure 18:
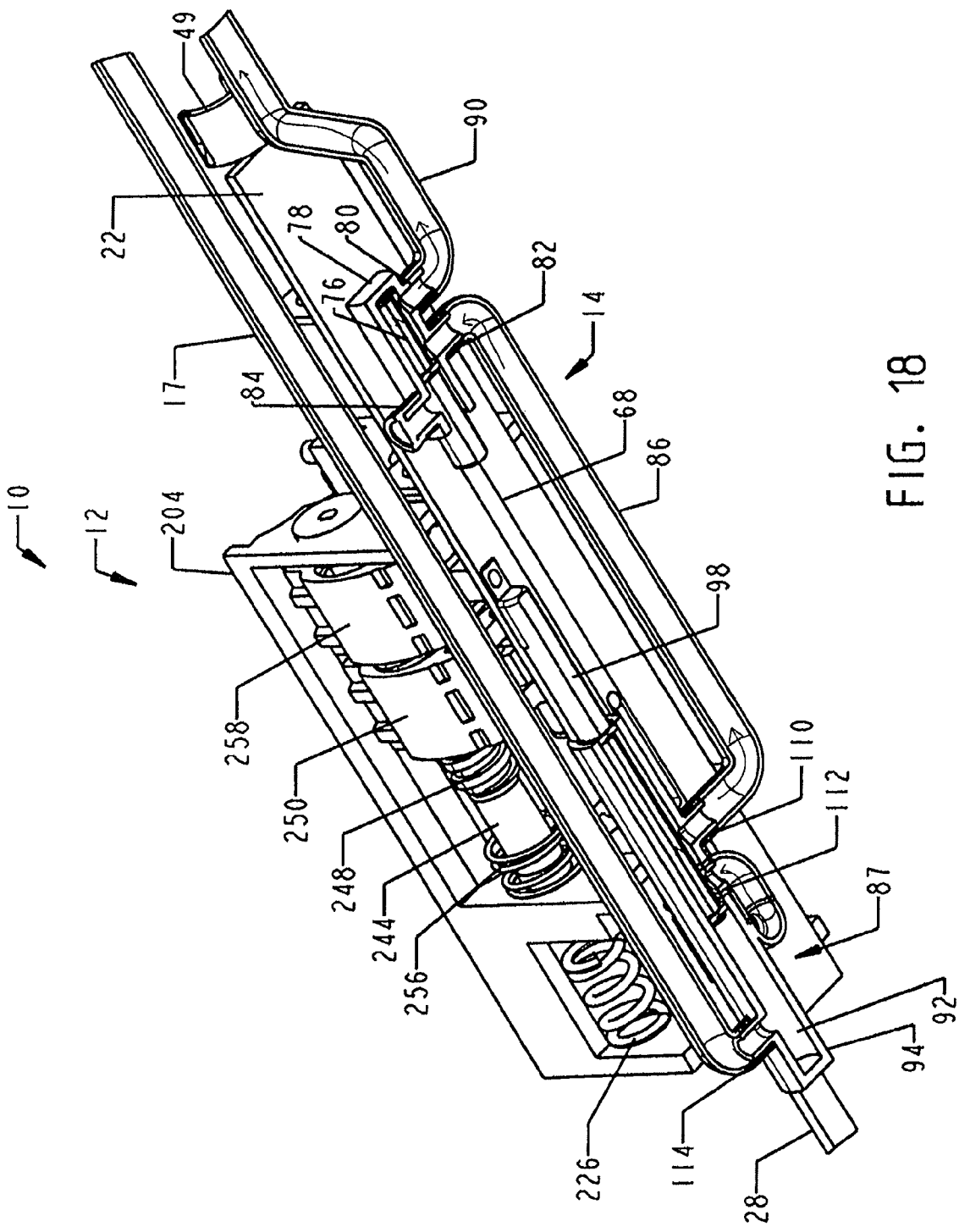
FIG. 18 is a bottom isometric view of the frame and dual carriage portion of the biopsy device of FIG. 1 with a horizontal portion cutaway made through the pneumatic components of the engaged disposable probe assembly with valving positioned such that vacuum is communicated to the lateral lumen.
Figure 19:
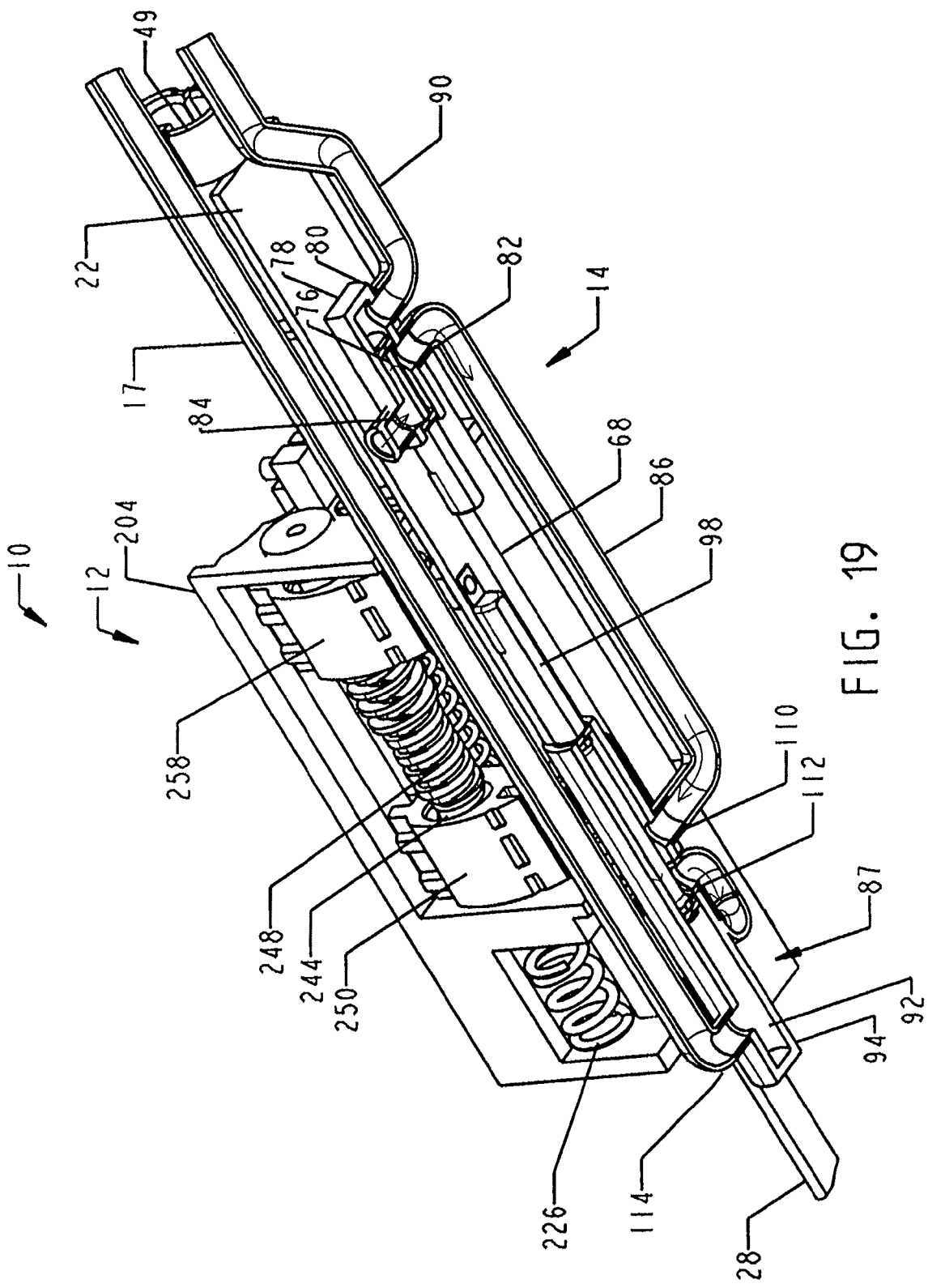
FIG. 19 is a bottom isometric view of the frame and dual carriage portion of the biopsy device of FIG. 1 with a horizontal portion cutaway made through the pneumatic components of the disposable probe assembly with valving positioned such that atmospheric pressure is communicated to the lateral lumen.
Figure 20:
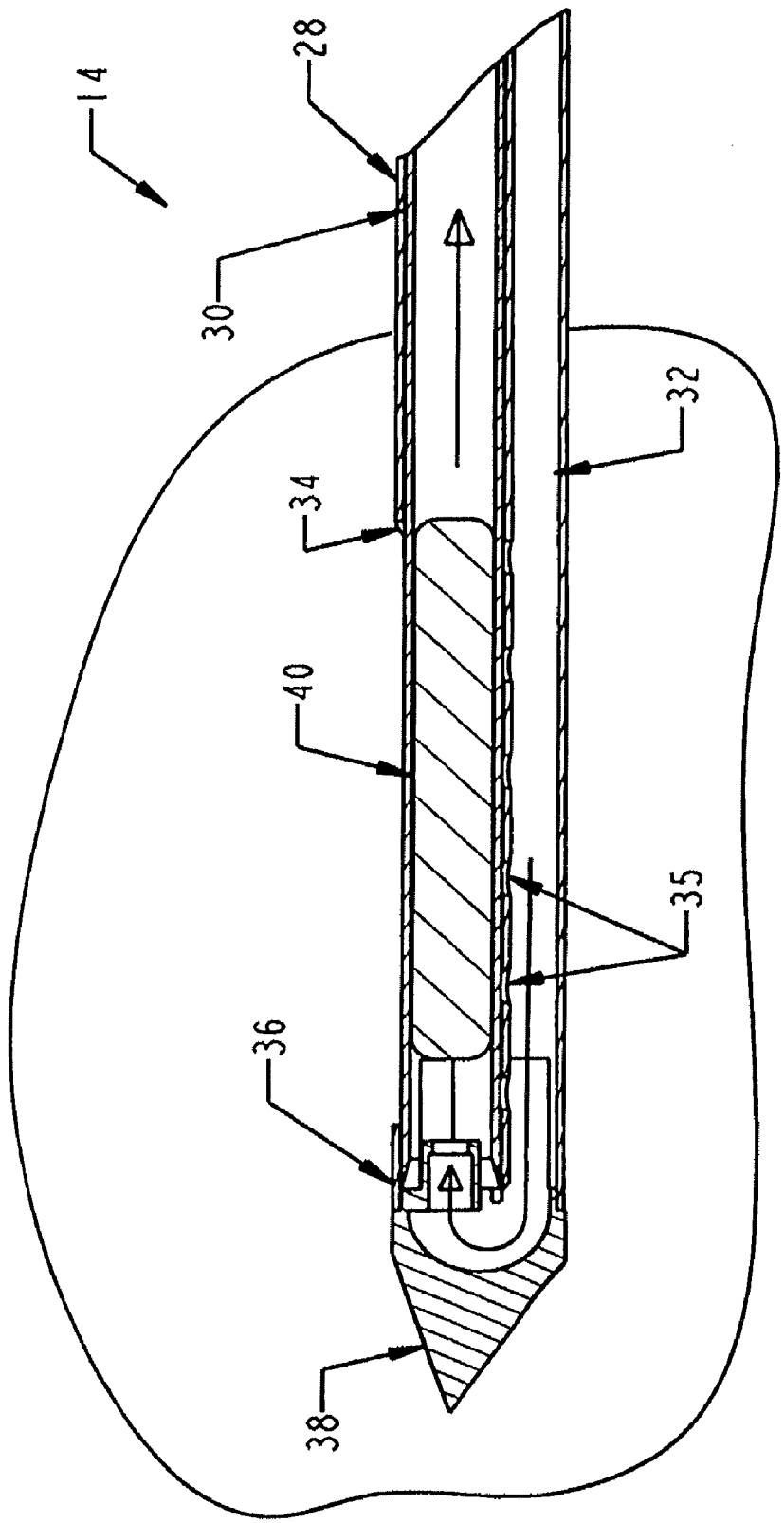
FIG. 20 is a left side view of the probe assembly of the biopsy device of FIG. 1 taken in longitudinal cross section exposing a cutter tube distally positioned after severing a tissue sample being retracted by vacuum assistance.
Figure 21:
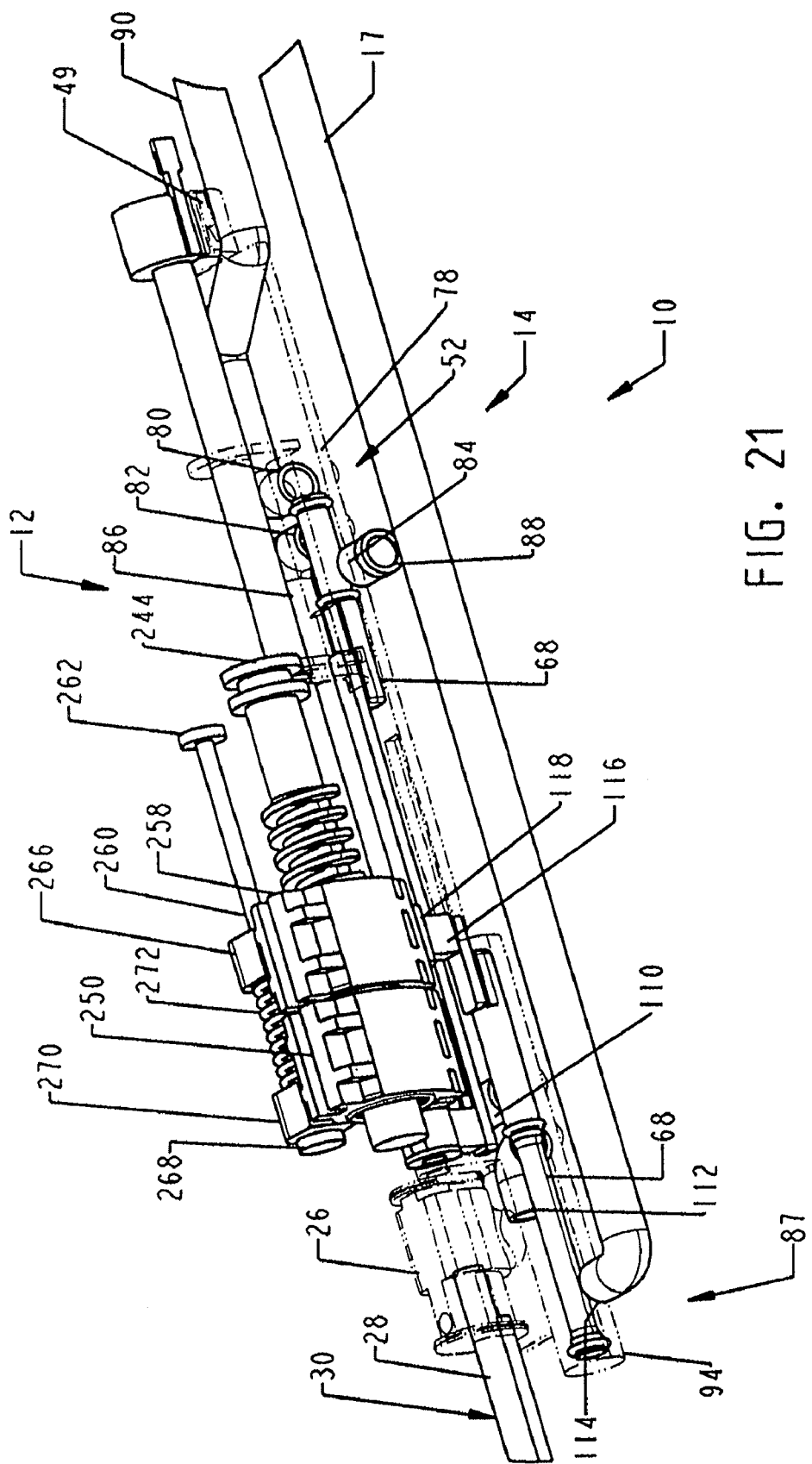
FIG. 21 is a left isometric view of portions of the biopsy device of FIG. 1 depicted to include the dual carriages in a distal position for saline flush and sleeve union in phantom and also depicted with the probe and pneumatic components of the disposable probe assembly.
Figure 22:
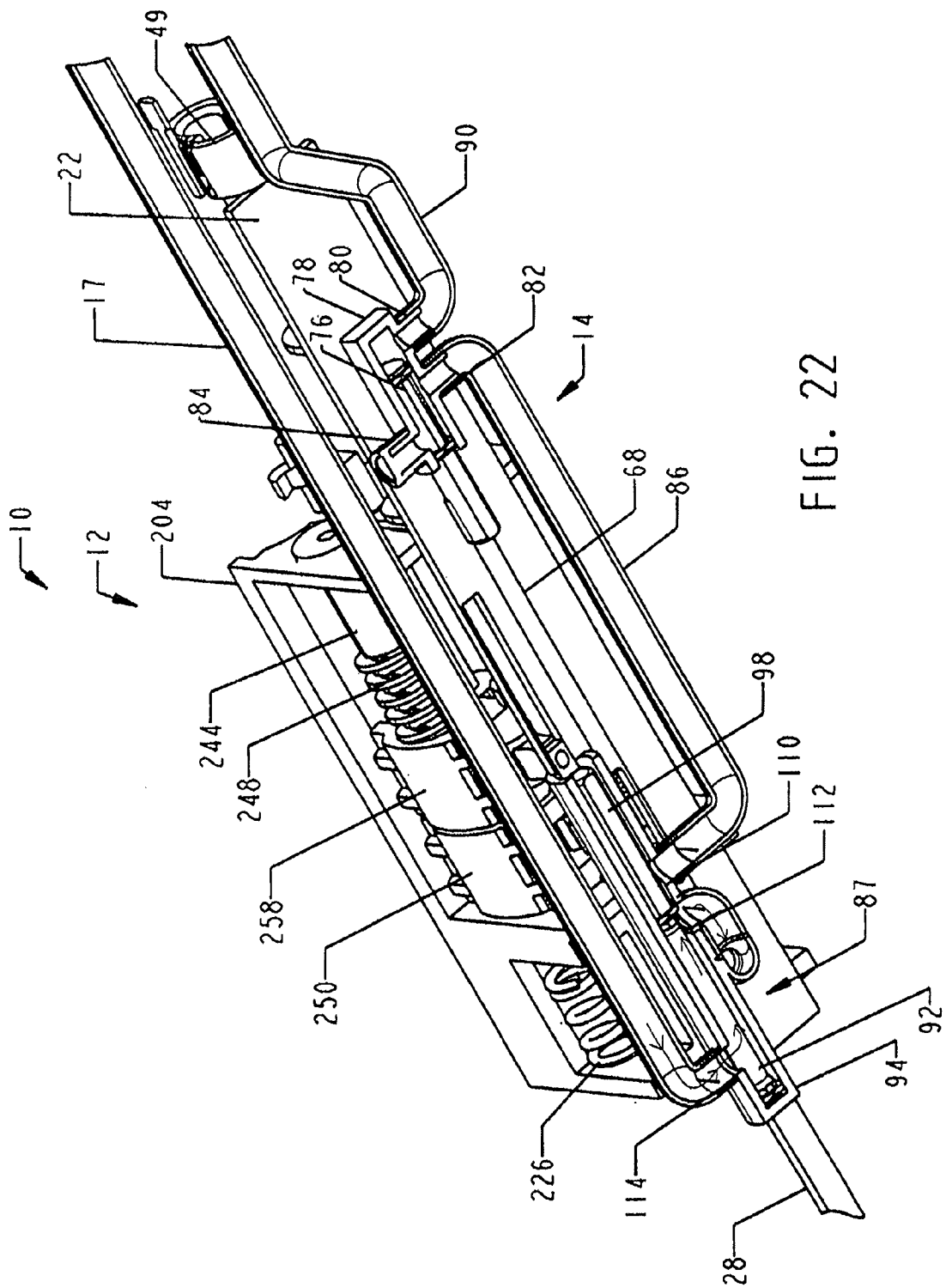
FIG. 22 is a bottom isometric view of the frame and dual carriage portion of the biopsy device of FIG. 1 with a horizontal portion cutaway made through the pneumatic components of the engaged disposable probe assembly with valving positioned such that saline is communicated to the lateral lumen.

With the probe assembly 28 positioned, the slide button 168 is moved proximally to move slide spur gear 176 into engagement with the gearbox input gear 196. Depression of the reverse motor rotation key 164 causes the distal carriage 250 to retract (FIG. 17). Thereby, the vacuum assist valve assembly 52 (FIG. 5) communicates vacuum through saline flush valve assembly 87 (FIG. 7) of the disposable probe assembly 14 (FIG. 18) through the vacuum lumen 32 to a now open side aperture 34 in the probe tube 30 (FIG. 4) to prolapse tissue. Vacuum is maintained by a lower pressure also communicating through the cutter tube 40 through the proximal sample stacker 48. Depression of the forward motor rotation key 162 (FIG. 1) distally translates the distal carriage 250 and thus the cutter tube 40 to sever a tissue sample (FIG. 20) as well as shifting the vacuum assist valve assembly 52 to a distal position (FIG. 6) that communicates an increased pressure (e.g., atmosphere) through the saline flush valve assembly 87 (FIG. 7) through the vacuum lumen 32 to the side aperture 34, allowing the vacuum through the cutter tube 40 to retract the tissue sample (FIG. 20).

At this point or after subsequent sample taking cycles, the surgeon my elect to flush tissue debris or coagulated blood from the vacuum lumen 32, side aperture 34 and cutter tube 40 of the probe assembly 28. By further depression of the forward motor rotation key 162, the distal carriage 250 advances slightly forward, drawing the proximal carriage 258 onto the lead screw threads 248, and thereafter the distal carriage 250 free wheels. Thereby, the flush valve assembly 87 switches from pneumatically coupling the lateral lumen 32 to the vacuum assist valve assembly 52 to coupling the saline supply (not shown) to the vacuum lumen 32. Thereby, the vacuum drawn through the cutter tube 40 causes saline (or other liquid provided) to be drawn through the vacuum lumen 32 and into a distal end of the cutter tube 40 and out of the disposable probe assembly 14, through proximal sample stacker 48 and then into the fluid collection canister (not shown) located near the vacuum pump. When the proximal carriage 250 is not fully distal, the flush valve 87 is positioned proximal of its fully distal position and prevents saline from communicating with the lateral lumen 32 of the probe assembly 28.

Control implementation may include sensing of the position of the distal carriage 250 such that motor operation stops distal travel of the distal carriage 250 prior to distal translation of the proximal carriage 258, requiring release of the forward motor rotation key 162 prior to actuating again to indicate a desire for saline flush. Alternatively, a separate override button (not shown) may be used that continues forward rotation of the lead screw 244 to effect the saline flush feature.

It should be appreciated that in the illustrative version, the distal carriage 250 does not freewheel in its proximal-most position. Instead, rotation of the motor is stopped as the distal carriage 250 is about to contact the proximal carriage 258 with closed-loop control based on an encoder (not shown) coupled to the DC motor 172 enabling accurate positioning of the motor output shaft 174. Alternatively, freewheeling may be incorporated at the proximal-most position of the distal carriage 250 by adding a section of no helical threads to the proximal end of the lead (translation) screw 244 equal to the longitudinal thickness of the distal carriage 250.

By virtue of the foregoing, with one-handed operation, a clinician is able to select between a plurality of ports (e.g., vacuum pressure, atmospheric pressure, saline supply) that can communicate with a side aperture 34 of a needle assembly 28 of core biopsy device 10. In particular, valve mechanisms are contained on the hand piece that need only selectively port a constant vacuum source without the necessity for a separate, expensive programmed control module. One advantage of such an economical capability is providing "on-demand" saline flush to the side aperture 34 (or distal opening) of the needle assembly 28. During normal tissue sampling, the side aperture 34 pressure levels transitions from vacuum during cutting to atmospheric pressure while the tissue sample is being transported proximally out of the reusable handpiece 12. Clearing tissue debris from the needle assembly 28 at the press of a saline push key 166 during the sample ensures proper operation so that the desired number of samples may be taken.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention may be alternatively described as a means for performing that element's function.

For example, one or more sensors may be incorporated into the hand piece 12 to sense the actual position of each carriage or to sense the particular disposable probe assembly assembled into the hand piece 12.

As another example, use of a proximal carriage for saline flush takes advantage of this additional motive device that is dedicated for sample retrieval in other versions of the disposable probe assembly (i.e., straw). In some applications consistent with the present invention where two carriages are not required or desired, an alternative saline valve selection may be incorporated where a separate electromechanical valve actuator may be incorporated that is not driven by the lead screw.

As an additional example, biasing the cutter tube 40 with a vacuum source advantageously assists in both prolapsing tissue as well as retracting tissue samples from the probe assembly 28. However, applications consistent with the present invention may include reversing the direction of fluid flow through the cutter tube and out of the lateral lumen 32. In addition, prolapsing of tissue may be alternatively achieved by closing the lateral lumen and allowing the vacuum bias through the cutter tube 40 to effect tissue prolapse. In addition, a pressurized liquid source may be directed by the flush valve assembly to forcibly push out a tissue sample or debris without the assistance of a vacuum bias on the cutter tube.

As yet a further example, while the illustrative versions advantageously utilize a single motor and a single lead screw to translate two carriages, applications consistent with aspects of the present invention may use two motors and two lead screws or one motor selectively coupled to one of two lead screws, each having a carriage.

As yet an additional example, while selective depression of the saline push key 166 provides clinical flexibility, it should be appreciated that the dual carriage lends itself to alternatively mechanizing automatic saline flush after each cutting cycle.

What is claimed is:
1. A biopsy device, comprising:
(a) a cannula having a transverse tissue receiving aperture;
(b) a cutter movable relative to the cannula to sever tissue protruding through the transverse tissue receiving aperture; and
(c) a first valve assembly, wherein the first valve assembly comprises:
(i) a first valve body having a first port, a second port, and a third port, wherein the first port is in fluid communication with either atmospheric air or a pressurized medium, wherein the second port is in fluid communication with the cannula, wherein the third port is in fluid communication with a vacuum source, and
(ii) a first actuator translatable relative to the first valve body, wherein the first actuator is movable between a proximal position and a distal position to selectively couple either the first port or the third port with the second port.

2. The biopsy device of claim 1, wherein the first valve body defines a bore, wherein the bore is in fluid communication with the first, second, and third ports.

3. The biopsy device of claim 2, wherein the first actuator comprises an elongate member slidably disposed within the bore.

4. The biopsy device of claim 1, wherein the first valve assembly further comprises one or more sealing members, wherein the one or more sealing members are configured to substantially seal the first port relative to the second port when the third port and the second port are in fluid communication.

5. The biopsy device of claim 4, wherein the one or more sealing members are further configured to substantially seal the third port relative to the second port when the first port and the second port are in fluid communication.

6. The biopsy device of claim 4, wherein the one or more sealing members comprise one or more o-rings.

7. The biopsy device of claim 6, wherein the first actuator comprises an elongate member having an exterior, wherein the one or more o-rings are disposed on the exterior of the elongate member, wherein the one or more o-rings are configured to translate with the elongate member.

8. The biopsy device of claim 1, wherein the cannula comprises a first lumen and a second lumen, wherein the first lumen is substantially parallel to the second lumen, wherein the transverse tissue receiving aperture opens into the first lumen.

9. The biopsy device of claim 8, wherein the cutter is slidably disposed within the first lumen.

10. The biopsy device of claim 8, wherein the second port is coupled with the second lumen of the cannula.

11. The biopsy device of claim 1, wherein the first port is positioned distally relative to the second port.

12. The biopsy device of claim 1, wherein the second port is positioned distally relative to the third port.

13. The biopsy device of claim 1, further comprising a fourth port in fluid communication with a source of saline, wherein the fourth port is selectively coupled with the cannula.

14. The biopsy device of claim 13, further comprising a second valve assembly, wherein the second valve assembly comprises:
(i) a second valve body, wherein the fourth port is part of the second valve body, wherein the second valve body further comprises a fifth port and a sixth port, wherein the fifth port is in fluid communication with the cannula, wherein the sixth port is in fluid communication with the first valve assembly, and
(ii) a second actuator translatable relative to the second valve body, wherein the second actuator is movable between a proximal position and a distal position to selectively couple either the fourth port or the sixth port with the fifth port.

15. The biopsy device of claim 14, further comprising a conduit providing fluid communication between the second port of the first valve assembly and the fifth port of the second valve assembly, such that the second port of the first valve assembly is in fluid communication with the cannula via the conduit and the second valve assembly.

16. The biopsy device of claim 15, wherein the second actuator is further configured to substantially seal the fifth port relative to the sixth port when the fourth port is coupled with the fifth port, thereby substantially sealing the second valve assembly and the cannula relative to the first valve assembly when the fourth port is coupled with the fifth port.

17. The biopsy device of claim 14, wherein the first actuator and the second actuator are translatable independently relative to each other.

18. A biopsy device, comprising:
  (a) a cannula having a transverse tissue sample aperture;
  (b) a cutter movable relative to the cannula to sever tissue protruding through the aperture; and
  (c) a valve assembly, wherein the valve assembly comprises:
    (i) a valve body having a first port, and a second port, wherein the first port is in fluid communication with either atmospheric air or a pressurized medium, wherein the second port is in fluid communication with the cannula, and
    (ii) an actuator translatable relative to the valve body, wherein the actuator is movable between a proximal position and a distal position to selectively couple the first port with the second port or seal the first port relative to the second port.

19. The biopsy device of claim 18, wherein the valve body defines a bore, wherein the actuator is slidably disposed within the bore, wherein the valve assembly further comprises at least one o-ring positioned between the actuator and the valve body, wherein the at least one o-ring is configured to substantially seal the first port relative to the second port based on the longitudinal position of the actuator within the valve body.

20. The biopsy device of claim 18, wherein the valve body further comprises a third port, wherein the third port is in fluid communication with a vacuum source, wherein the actuator is further operable to selectively couple the second port with the third port based on the longitudinal position of the actuator relative to the valve body.

* * * * *